United States Patent [19]
Farnham et al.

[11] Patent Number: 5,243,025
[45] Date of Patent: Sep. 7, 1993

[54] REACTION OF PERFLUOROOLEFINS WITH BIS(SILYL) ETHERS TO PRODUCE FLUORINATED COMPOUNDS

[75] Inventors: William B. Farnham, Wilmington; Mario J. Nappa, Newark, both of Del.

[73] Assignee: E. I. Du Pont de Nemours and Company, Wilmington, Del.

[21] Appl. No.: 645,030

[22] Filed: Jan. 23, 1991

Related U.S. Application Data

[63] Continuation-in-part of Ser. No. 243,396, Sep. 12, 1988, abandoned.

[51] Int. Cl.$^5$ ............................................. C08G 67/00
[52] U.S. Cl. .................................... 528/392; 528/401; 528/14; 528/21; 528/22; 528/23; 528/25; 528/33
[58] Field of Search .................... 526/287; 528/14, 21, 528/22, 23, 25, 33, 392, 401

[56] References Cited

U.S. PATENT DOCUMENTS

| | | | |
|---|---|---|---|
| 3,397,191 | 8/1968 | Beckerbauer | 526/247 |
| 3,497,563 | 2/1970 | Gash | 260/611 |
| 3,549,606 | 12/1970 | Gash | 260/91.1 |
| 3,803,110 | 4/1974 | Richards | 526/247 |
| 3,840,603 | 10/1974 | Anderson | 528/392 |
| 4,085,137 | 4/1978 | Mitsch et al. | 526/247 |
| 4,474,932 | 11/1984 | Bier et al. | 528/25 |
| 4,568,773 | 2/1986 | Ohmori et al. | 568/615 |
| 4,687,821 | 8/1987 | Ezzell et al. | 526/247 |

OTHER PUBLICATIONS

Hans R. Kricheldorf and Gerhard Bier, Journal of Polymer Science, Polymer Chemistry Edition, vol. 21, 2283–2289 (1983).

Hans R. Kricheldorf and Gerhard Bier, Polymer, vol. 25, 1151 (1984).

D. G. Saunders, Synthesis No. 5, Communications, 377 (1988).

*Primary Examiner*—Ralph H. Dean, Jr.

[57] ABSTRACT

A reaction of perfluoroolefins with bis(silyl) ethers to produce novel partially fluorinated and perfluorinated copolymers and macrocyclic compounds is disclosed.

6 Claims, No Drawings

REACTION OF PERFLUOROOLEFINS WITH BIS(SILYL) ETHERS TO PRODUCE FLUORINATED COMPOUNDS

CROSS-REFERENCE TO RELATED APPLICATION

This application is a continuation-in-part of application U.S. Ser. No. 07/243,396, filed Sep. 12, 1988, now abandoned.

BACKGROUND OF THE INVENTION

1. Field of the Invention

Polymers with high levels of fluorine have novel properties including chemical and thermal resistance.

This invention provides a novel route to fluorinated polyethers by reacting perfluoroolefins with bis(silyl) ethers in the presence of a catalyst to produce partially fluorinated and perfluorinated copolymers and macrocyclic compounds, partially fluorinated bis(vinyl) ethers and perfluorinated bis(alkyl) ethers. The compositions of this invention are useful in vapor phase soldering, as lubricants and as heat stable oils and greases.

2. Technical Background

Hans R. Kricheldorf and Gerhard Bier, Journal of Polymer Science, Polymer Chemistry Edition, Vol. 21, 2283-2289 (1983) disclose the condensation polymerizations of bis(4-fluorophenyl) sulfone with the bis trimethylsilyl derivatives of bisphenol-A, 4,4'-dihydroxydiphenyl, 4,4'-dihydroxydiphenyl sulfone, 1,5-dihydroxynaphthalene, 3-hydroxybenzoic acid, and 4-hydroxybenzoic acid. These polycondensations were only successful when potassium or cesium fluoride was used as a catalyst.

Hans R. Kricheldorf and Gerhard Bier, Polymer, Vol. 25, 1151 (1984) disclose the bulk condensations of 4,4'-difluorobenzophenone and various silylated bisphenols at 220° C.-320° C. with cesium fluoride as a catalyst.

U.S. Pat. No. 4,474,932 discloses and claims a process for the preparation of aromatic ethers or polyethers by reacting aromatic fluorine compounds, in which one or more fluorine substituents are attached to an aromatic nucleus, with trialkylsilyl derivatives of phenols, in which one or more trialkylsilyl groups are attached to the residue of a mono or polyphenol, or by reacting trialkylsilyl derivatives of fluorophenols with elimination of trialkylfluorosilane.

D. G. Saunders, Synthesis, No. 5, Communications, 377 (1988) discloses the reaction of aryl silyl ethers with alkyl halide, or activated aryl halide, and tetrabutylammonium fluoride, to give alkyl aryl ethers or diaryl ethers, respectively. Alkyl silyl ethers under the same or related reaction conditions give mainly the corresponding alcohol, and only very low yields of the ether.

U.S. Pat. No. 3,549,606 claims fluoroalkyl ether polymers of alicyclic fluoroolefins comprised of repeating units of the structure:

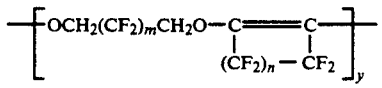

wherein n=1-7, y is at least 2 and m is a number from 1-12.

U.S. Pat. No. 3,497,563 claims ethers of the formula:

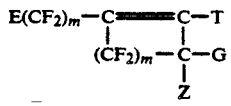

wherein:

E is selected from the group consisting of hydrogen, fluorine and —CH$_2$OH and may be —CH$_2$OH only when T, G and Z are halogen;

G is selected from the group consisting of fluorine and —OCH$_2$(CF$_2$)$_m$D and is fluorine when T is —CH$_2$(CF$_2$)$_n$D;

T is selected from the group consisting of bromine, chlorine and —OCH$_2$(CF$_2$)$_m$D and is a halogen when G and Z are —OCH$_2$(CF$_2$)$_m$D;

Z is selected from the group consisting of fluorine and —OCH$_2$(CF$_2$)$_m$D and is fluorine when T is —OCH$_2$(CF$_2$)$_m$D;

D is selected from the group consisting of hydrogen and fluorine; and n is a number from 1-7 and each m expression is a number from 1 to 12. That invention also claims a method for producing an unsaturated fluorine containing alicyclic ether by reacting cyclic olefin of the formula:

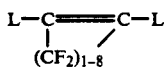

where L is selected from the group consisting of fluorine, bromine and chlorine with a fluoroalkanol, in the presence of an alkali metal hydroxide.

SUMMARY OF THE INVENTION

The present invention provides a polymer consisting essentially of the repeat unit:

wherein:

R is a diradical of the formula —C$_x$H$_{2x-y}$F$_y$—, where x is an integer from 2 to 20, y is 0 or an integer from 1 to 2x for a given value of x, but with the additional proviso that the carbon atoms containing the free valence of the diradical not be attached to fluorine atoms, and when x is a integer from 4 to 20 some of the carbon atoms may be internally interrupted with oxygen atoms forming ether structures and with the proviso that the oxygen atoms be separated by two or more carbon atoms; —C$_6$H$_{4-a}$F$_a$—, wherein a is 0, 1, 2, 3, or 4; —C$_{10}$H$_{6-b}$F$_b$—, wherein b is 0 or an integer from 1 to 6, with the proviso that the radical bonds are not on adjacent carbon atoms; —C$_{12}$H$_{8-c}$F$_c$—, wherein c is 0 or an integer from 1 to 8, with the proviso that the radical bonds are not on adjacent carbon atoms; and —CH$_{4-d}$F$_d$—R$^1$—C$_6$H$_{4-e}$F$_e$—, wherein d and e are independently 0 or an integer from 1 to 4, R$^1$ is —C$_x$H$_{2x-f}$F$_f$—, wherein f is 0 or an integer from 1 to 2x;

R$_f^1$ and R$_f^2$ are independently —C$_z$CF$_{2z+1}$, wherein z is an integer from 1 to 10; or R$_f^1$ and R$_f^2$ taken together where R$_f^1$ and R$_f^2$ in the cis configuration are —(CF$_2$-

$)_m$—, wherein m is 2, 3 or 4, provided that when $R_f^1$ and $R_f^2$ are as defined, then R shall not be —CH$_2$(CF)$_s$CH$_2$— where s is an integer from 1 to 12, C$_6$F$_5$—, C$_{10}$F$_7$— or C$_{12}$F$_9$—.

The invention additionally provides polymers consisting essentially of the repeat unit:

   (B)

wherein $R_f^1$ is as defined above; $R^8$ is R as defined above with the proviso that one of the carbon atoms adjacent to the carbon atoms containing the free valence of the diradical be attached to at least two fluorine atoms.

The invention additionally provides a macrocyclic compound of the structures:

   (C)

   (C')

wherein $R_f^1$, $R_f^2$, R and $R^8$ are as defined above and w is 1, 2, 3 or 4.

The invention additionally provides bis(vinyl) ethers of the structures:

(D) $R_f^1(F)C$=$C(R_f^2)OROC(R_f^2)$=$C(F)R_f^1$,
(E) $R_f^1(F)C$=$C(F)OR^8OC(F)$=$C(F)R_f^1$, and
(E') $R_f^1R_f^2C$=$C(R_f^6)OR^8OC(R_f^6)$=$CR_f^2R_f^1$ wherein $R_f^1$, $R_f^2$, R and $R^6$ are defined above and $R_f^6$ is the same as $R_f^1$.

The invention additionally provides a polymer consisting essentially of the repeat unit:

(J) —[(R$_f^4$)(F)CC(F)(R$_f^5$)OR$_f^3$O]— wherein:

$R_f^3$ is a diradical selected from —C$_x$F$_{2x}$—, where x is an integer from 2 to 20; when x is an integer from 4 to 20, some of the carbon atoms may be internally interrupted with oxygen atoms forming ether structures, with the proviso that the oxygen atoms be separated by two or more carbon atoms; $R_f^4$ and $R_f^5$ are independently selected from C$_z$F$_{2z+1}$, z is an integer from 1 to 10 or $R_f^4$ and $R_f^5$ taken together are —(CF$_2$)—$_m$, and m is 2, 3 or 4, and wherein no olefinic unsaturation is present in the polymer.

The invention additionally provides a polymer consisting essentially of the repeat unit:

(K) —[CF(CF$_2$R$_f^4$)OR$_f^3$O]— wherein $R_f^3$ and $R_f^4$ are as defined above.

The invention additionally provides acyclic compound of the structure:

   (L)

and

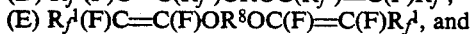   (L')

wherein $R_f^3$, $R_f^4$, $R_f^5$, and w are as defined above.

The invention additionally provides a bis(perfluoroalkyl)ether of the structure:

(M) $R_f^4CF_2CF(R_f^5)OR_f^3OCF(R_f^5)CF_2R_f^4$,
(N) $R_f^4CF_2CF_2OR_f^3OCF_2CF_2R_f^4$, and
(N') $R_f^4R_f^5CFCF(R_f^6)OR_f^3OCF(R_f^6)CFR_f^4R_f^5$ wherein $R_f^3$, $R_f^4$, $R_f^5$, and $R_f^6$ are as defined above.

In addition, the invention provides processes for the preparation of the above compositions, A, B, C, C', D, E and E' by a polycondensation reaction of silyl ethers and perfluoroolefins, or, in some cases, with a bis(vinyl) ether prepolymer in place of the perfluoroolefin, at selected dilutions, in the presence of a suitable catalyst which may be a source of fluoride ion, such as, but not limited to CsF, tris(dialkylamino)sulfonium difluorotrimethylsilicate, tetrabutylammonium fluoride, tris(dialkylamino)sulfonium bifluorides. The reaction will also proceed with other catalysts which are not sources of fluoride ion including M$^+$ZCO$_2$—, M$^+$OC$_6$H$_4$NO$_2$— and M$^+$ZSO$_2$— where Z is a linear or branched alkyl group containing from 1 to 10 carbon atoms or phenyl group and M$^+$ is any cation preferably (Z'$_2$N)$_3$S$^+$. Z' is a linear or branched alkyl group containing from 1 to 10 carbon atoms.

The temperature of the reactions to prepare the above compositions can range from about $-50°$ C. to $120°$ C. The processes can proceed in the presence of a solvent that does not react with reagents or products or in the absence of any solvent.

Compounds J, K, L, L', M, N, and N' are prepared by reacting elemental fluorine with compositions A-E'.

DETAILS OF THE INVENTION

The novel reaction of bis(silyl) ethers with perfluorinated olefins has been used to synthesize a series of partially fluorinated polymers, bis(vinyl) ethers and macrocyclic structures. These partially fluorinated compounds can in turn react with elemental fluorine to produce a series of novel perfluoro polymers, bisperfluoroalkyl ethers, and perfluoromacrocyclic structures.

The partially fluorinated products have utility as heat stable liquids and greases. The perfluorinated structures have utility as lubricants and heat stable fluids.

By a polymer herein is meant a compound with two or more repeat units that is not cyclic.

In the polymer (A), the groups —C$_6$H$_{4-a}$F$_a$—, —C$_6$H$_{4-d}$F$_d$— and —C$_6$H$_{4-e}$F$_e$— means a (fluorinated) phenylene group, the group —C$_{10}$H$_{6-b}$F$_b$— means a (fluorinated) naphthylylene group, and the group —C$_{12}$H$_{8-c}$F$_c$— means a biphenylene group. With the proviso that the radical bonds are not on adjacent (ring) carbon atoms, the phenylene group could be, for example, meta- or paraphenylene.

The invention provides a process for the preparation of (A) by a polycondensation reaction of R$^2$R$^3$R$^4$SiOROSiR$^5$R$^6$R$^7$ (F) and $R_f^1(F)C$=$C(F)R_f^2$ (G) in the presence of a catalyst, wherein R$^2$, R$^3$, R$^4$, R$^5$, R$^6$, and R$^7$ are independently CH$_3$— or C$_2$H$_5$— or one of R$^2$, R$^3$, R$^4$, R$^5$, R$^6$, and R$^7$ may be C$_6$H$_5$— with the remainder of the groups being independently CH$_5$ or C$_2$H$_5$—, and R, $R_f^1$ and $R_f^2$ are as defined above In the above process, a bis(vinyl) ether [which can be considered a prepolymer] of structure $R_f^1(F)C$=$C(R_f^2)ORO(R_f^2)C$=$C(F)R_f^1$ can be used in place of $R_f^1(F)C$=$C(F)R_f^2$ in the polymerization process. The use of a prepolymer offers the advantage of more precise measurement of starting materials and higher degree of control over olefin reactivity.

The polymerization reaction is normally done in a solvent such as glyme or tetrahydrofuran. However, any organic or inorganic compound may be used as solvent so long as the compound does not interact with the starting materials or interfere with the polymerization reaction under reaction conditions. The reaction can be done in the absence of solvent if so desired.

The molar ratio of perfluoroolefin to bis(silyl) ether can range from 0.9 to 2.5. The molar ratio of bis(vinyl) ether to bis(silyl) ether can range from 0.9 to 1.5. The molar ratio of bis(silyl) ether to catalyst can range from 4 to 10,000. The concentration of bis(silyl) ether in solution is greater than or equal to 0.01M. The temperature of the polymerization reaction can range from −50° C. to 120° C. The polymer can be recovered by removing solvent and volatile by-products by heating under vacuum.

Preferred bis(silyl) ethers are those in which $R^2$, $R^3$, $R^4$, $R^5$, $R^6$, and $R^7$ are —$CH_3$ and R is —$CH_2(CF_2)_3CH_2$—, —$CH_2(CF_2)_2O[CF(CF_3)CF_2O]_hCF(CF_3)CH_2$— where h is 0, 1, 2, 3 or 4, $(CH_2)_4$, —$CH_2(CF_2)_2OCF(CF_3)CF_2OCF(CF_3)CH_2$—, or —p—$C_6H_4C(CF_3)_2C_6H_4$—p—.

Preferred perfluoroolefins are those in which $R_f^1$ and $R_f^2$ are —$CF_3$ and where $R_f^1$ and $R_f^2$ taken together are —$(CF_2)_2$—.

The invention additionally provides a process for the preparation of (B) by a polycondensation reaction of $R^2R^3R^4SiOR^8OSiR^5R^6R^7$ (H) and $R_f^1(F)C=CF_2$ (I) in the presence of a catalyst, preferably CsF. $R_f^1$, $R^2$, $R^3$, $R^4$, $R^5$, $R^6$, $R^7$, and $R^8$ are as defined above.

Bis(vinyl) ethers [prepolymer] of structure $R_f^1(F)C=C(F)OR^8O(F)C=C(F)R_f^1$ can be used in place of $R_f^1(F)C=CF_2$ in the polymerization process.

The polymerization reaction conditions and solvents are as described for ("A") above. Preferred conditions for the polymerization reaction to yield B are when the temperature range is −20° C. to +10° C., the catalyst is CsF and the solvent is glyme or THF.

Preferred bis(silyl) ethers are those in which $R^2$, $R^3$, $R^4$, $R^5$, $R^6$, and $R^7$ are —$CH_3$ and $R^8$ is —$CH_2(CF_2)_3CH_2$—, and —$CH_2(CF_2)_2O[CF(CF_3)CF_2O]_hCF(CF_3)CH_2$— with h 0, 1, 2, 3 or 4.

Preferred perfluoroolefins are those in which $R_f^1$ is —$CF_3$, or —$C_2F_5$.

The invention additionally provides macrocyclic compounds of the following structures:

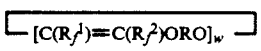

(C)

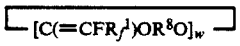

(C')

where $R_f^1$, $R_f^2$, R and $R^8$ are as defined above and w is 1 to 4.

The invention additionally provides a process for the preparation of (C) by a condensation reaction of $R^2R^3R^4SiOROSiR^5R^6R^7$ (F) and $R_f^1(F)C=C(F)R_f^2$ (G) in dilute solutions in the presence of a catalyst.

The preferred catalysts are CsF and tris(dialkylamino)sulfonium difluorotrimethyl silicate. $R_f^1$, $R_f^2$, R, $R^2$, $R^3$, $R^4$, $R^5$, $R^6$, and $R^7$ are as defined above.

A bis(vinyl) ether of structure $R_f^1(F)C=C(R_f^2)ORO(R_f^2)C=C(F)R_f^1$ can be used in place of $R_f^1(F)C=C(F)R_f^2$ in the cyclization process and is preferred for highest yields. However, when bis(vinyl) ether is used only the macrocyclic structures with w=2 or 4 can be synthesized.

The cyclization reaction is normally done in a solvent such as glyme or tetrahydrofuran. However, any organic or inorganic compound may be used as solvent so long as the compound does not interact with the starting materials or interfere with the cyclization reaction under reaction conditions. The molar ratios are as above except that the concentration of bis(silyl) ether in solution can range from 0.001M to 0.1M.

The temperature of the cyclization reaction can range from −50° C. to 120° C.

The cyclic compound can be recovered by removing solvent and volatile by-products by heating under vacuum. The cyclic compound can be purified by conventional methods such as vacuum distillation, chromatography and/or crystallization.

Preferred bis(silyl) ethers are those in which $R^2$, $R^3$, $R^4$, $R^5$, $R^6$, and $R^7$ are —$CH_3$ and R is —$CH_2(CF_2)_3CH_2$—, —$CH_2(CF_2)_2O[CF(CF_3)CF_2O]_hCF(CF_3)CH_2$— where h is 0, 1, 2, 3 or 4, —$(CH_2)_4$—, and —$CH_2(CF_2)_2OCF(CF_3)CF_2OCF(CF_3)CH_2$—.

Preferred perfluoroolefins are those in which $R_f^1$ and $R_f^2$ taken together ($R_f^1$ and $R_f^2$ in cis configuration) are —$(CF_2)_2$—.

The invention additionally provides a process for the preparation of (C') by a condensation reaction of $R^2R^3R^4SiOR^8OSiR^5R^6R^7$ (H) and $R_f^1(F)C=CF_2$ (I) in dilute solution in the presence of a catalyst such as CsF. $R_f^1$, $R^2$, $R^3$, $R^4$, $R^5$, $R^6$, $R^7$, and $R^8$ are as defined above.

Bis(vinyl) ethers of structure $R_f^1(F)C=C(F)OR^8O(F)C=C(F)R_f^1$ can be used in place of $R_f^1(F)C=CF_2$ in the cyclization process and is preferred for highest yields. However, when bis(vinyl) ethers are used only macrocyclic compounds with w=2 or 4 can be synthesized.

The cyclization reaction is normally done in a solvent such as glyme or tetrahydrofuran in dilute solutions, as described for (C) above.

Preferred bis(silyl) ethers are those in which $R^2$, $R^3$, $R^4$, $R^5$, $R^6$, and $R^7$ are —$CH_3$ and $R^8$ is —$CH_2(CF_2)_3CH_2$—, and —$CH_2(CF_2)_2O[CF(CF_3)CF_2O]_hCF(CF_3)CH_2$— where h is 0, 1, 2, 3 or 4.

Preferred perfluoroolefins are those in which $R_f^1$ is —$CF_3$ or —$C_2F_5$.

The invention additionally provides a process for the preparation of (D) by a condensation reaction of $R^2R^3R^4SiOR^8OSiR^5R^6R^7$ (F) and $R_f^1(F)C=C(F)R_f^2$ (G) in the presence of a catalyst. The preferred catalysts are CsF and tris(dialkylamino)sulfonium difluorotrimethyl silicate. $R_f^1$, $R_f^2$, R, $R^2$, $R^3$, $R^4$, $R^5$, $R^6$, and $R^7$ are as defined above.

The condensation reaction is normally done in a solvent such as glyme or tetrahydrofuran. However, any organic or inorganic compound may be used as solvent so long as the compound does not interact with the starting materials or interfere with the condensation reaction under reaction conditions.

The molar ratio of bis(silyl) ether to catalyst can range from 4 to 10,000. The molar ratio of perfluoroolefin to bis(silyl) ether can range from 2.2 to 12. The concentration of bis(silyl) ether in solution is greater than or equal to 0.01M. The temperature of the condensation reaction can range from −50° C. to 120° C. The prepolymer can be recovered by removing solvent and volatile by-products by heating under vacuum. The prepolymer can be purified by vacuum distillation.

Preferred bis(silyl) ethers are those in which $R^2$, $R^3$, $R^4$, $R^5$, $R^6$, and $R^7$ are —$CH_3$ and R is —$CH(CH_3)CH_2$—, —$(CH_2)_3$—, —$(CH_2)_4$—, —$(CH_2)_5$—, —$(CH_2)(CF_2)_3CH_2$—, —$CH_2(CF_2)_2OCF(CF_3)F_2OCF(CF_3)CH_2$—, —$CH_2(CF_2)_2O[CF(CF_3)C$—

$F_2O]_hCF(CF_3)CH_2$— where h is 0, 1, 2, 3 or 4, and —(p—$C_6H_4$)C($CF_3$)$_2$(p—$C_6H_4$)—. Preferred perfluoroolefins are those in which $R_f^1$ and $R_f^2$ taken together are —(CF$_2$)$_2$—, —(CF$_2$)$_3$—; $R_f^1$ and $R_f^2$ are —CF$_3$.

The invention additionally provides a process for the preparation of (E) by a condensation reaction of $R^2R^3R^4SiOR^8OSiR^5R^6R^7$ (H) with excess $R_f^1(F)C=CF_2$ (I) in the presence of a catalyst such as CsF, wherein $R_f^1$, $R^2$, $R^3$, $R^4$, $R^5$, $R^6$, and $R^7$ are as defined above.

The reaction is normally done in a solvent and with molar ratios as described for (D).

Preferred bis(silyl) ethers are those in which $R^2$, $R^3$, $R^4$, $R^5$, $R^6$, and $R^7$ are —CH$_3$ and $R^8$ is —CH$_2$(CF$_2$)$_3$CH$_2$—, and —CH$_2$(CF$_2$)$_2$O[CF(CF$_3$)CF$_2$O]$_h$CF(CF$_3$)CH$_2$— where h is 0, 1, 2, 3, or 4.

Preferred perfluoroolefins are those in which $R_f^1$ is —CF$_3$, —C$_2$F$_5$.

The invention additionally provides a process for the preparatin of (E') by a condensation reaction of $R^2R^3R^4SiOR^8OSiR^5R^6R^7$ (F) and $R_f^1R_f^2C=C(F)R_f^6$ (Q) in the presence of a catalyst. The preferred catalysts are CsF and tris(dialkylamino)sulfonium difluorotrimethyl silicate. $R_f^1$, $R_f^2$, R, $R^2$, $R^3$, $R^4$, $R^5$, $R^6$, $R^7$ and $R^8$ are as defined above.

The condensation reaction is normally performed in a solvent under the conditions and with molar concentrations as for (E) above.

Preferred bis-silyl ethers are those in which $R^2$, $R^3$, $R^4$, $R^5$, $R^6$, and $R^7$ are —CH$_3$ and R is —CH$_2$(CF$_2$)$_3$CH$_2$—, —CH$_2$(CF$_2$)$_2$OCF(CF$_3$)CF$_2$OCF(CF$_3$)CH$_2$—, —CH$_2$(CF$_2$)$_2$O[CF(CF$_3$)CF$_2$O]$_h$CF(CF$_3$)CH$_2$— where h is 0, 1, 2, 3 or 4, and —(p—$C_6H_4$)C(CF$_3$)$_2$(p—$C_6H_4$)—.

Preferred perfluoroolefins are those in which $R_f^1$ and $R_f^2$ are —CF$_3$— and $R_f^6$ is —CF$_3$CF$_2$—.

These bis(vinyl) ethers can also be used as intermediates for further polymerization with bis(silyl) ethers but the structure of the polymer is unknown.

(J) is prepared by reacting (A) with elemental fluorine when R, as contained in (A), is —$C_xH_{2x-y}F_y$—, as defined above. The fluorination procedure includes dissolving the intermediate in an inert solvent, purging the system with an inert gas to expel dissolved oxygen, cooling or heating the mixture to a proper reaction temperature and passing the fluorine gas in an oxygen-free inert gas stream through the solution. The solution is irradiated by means of an ultraviolet lamp. All fluorination processes herein result in the replacement of all hydrogen in the polymer with fluorine, and fluorination of all olefinic bonds to fluorinated saturated alkyl groups.

(K) is prepared by reacting (B) with elemental fluorine, when $R^8$, as contained in (B), is —$C_xH_{2x-y}F_y$—, as defined above. The fluorination procedure is performed as described for (J) above.

(L) is prepared by reacting (C) with elemental fluorine when R, as contained in (C), is —$C_xH_{2x-y}F_y$—, as defined above. The fluorination procedure is performed as described for (J) above.

(L') is prepared by reacting (C') with elemental fluorine, when $R^8$, as contained in (C'), is —$C_xH_{2x-y}F_y$—, as defined above. The fluorination procedure is performed as described for (J) above.

(M) is prepared by reacting (D) with elemental fluorine, when R, as contained in (D), is —$C_xH_{2x-y}F_y$—, as defined above.

(N) is prepared by reacting (E) with elemental fluorine, when $R^8$, as contained in (E), is —$C_xH_{2x-y}F_y$—, as described above.

(N') is prepared by reacting (E') with elemental fluorine, when R, as contained in (E'), is —$C_xH_{2x-y}F_y$—, as described above. The fluorination procedures for M, N and N' are performed as described for (J) above.

The macrocyclic structures C, and C' can interact with F$^-$ to form macrocyclic anions. The F$^-$ is bound to the cyclic structure by multiple C—H-anion interactions. The macrocyclic anions have been shown to be catalysts for the condensation reactions described in this application and for group transfer polymerization of methyl methacrylate.

EXAMPLES

Experimental

Fluorine chemical shifts are reported in ppm from CFCl$_3$. Spectra were recorded on a Nicolet NT200 spectrometer at 188.2 MHz. $^1$H NMR spectra were recorded on a GE QE-300 spectrometer, and chemical shifts are reported relative to tetramethylsilane at 0 ppm. Infrared spectra were recorded on a Perkin-Elmer 983G infrared spectrometer.

Mass spectral data were obtained using VG 7070-HS (with Varian Vista 6000 GC), VG 70-SE (with HP 5790 GC), VG ZAB-2F (high resolution), or VG ZAB-E (low resolution) instruments.

Gas chromatography was done using a Hewlett Packard 5890 instrument with 25 m × 0.2 mm HPl cross-linked methyl silicone capillary column, operating at 60°–250° C. (method 1).

Molecular weights (M$_w$ and M$_n$) were determined by size exclusion chromatography using polystyrene standards.

Solvents with minimum water concentrations were preferred for the reactions described herein. Tetrahydrofuran (THF), dimethoxyethane (glyme), and ether were distilled from sodium/benzophenone and stored under nitrogen. Other solvents were distilled and stored over activated molecular sieves.

Unless indicated otherwise, all reactants are either known compounds or can be prepared by known methods. All reactions were carried out in an atmosphere of dry nitrogen, and manipulations of hygroscopic or water sensitive catalysts were done in a Vacuum Atmospheres drybox. Low-boiling fluoroolefins were transferred to gas traps and measured by volume unless described otherwise.

EXPERIMENT 1

Preparation of (CH$_3$)$_3$SiO(CH$_2$)$_2$OSi(CH$_3$)$_3$

Hexamethyldisilazane (HMDS) (104 g, 0.64 mol) was added to distilled ethylene glycol (40 g, 0.64 mol) and the mixture was heated at 80° C. for 18 h. Distillation gave 103 g of colorless oil, bp 88° C./50 mm. Although the first portion to be collected was contaminated with lower-boiling materials, the latter portion was of high purity (99% by GC; methyl silicone gum, 80°–225° C.). $^1$H NMR (CDCl$_3$): 3.60 (s, 4H), 0.13 (s, 18H) consistent with the assigned structure.

EXPERIMENT 2

Preparation of (CH$_3$)$_3$SiO(CH$_2$)$_3$OSi(CH$_3$)$_3$ 1,3-Propanediol (47.8 g, 0.63 mol) was placed in a 500 mL 3-necked RB flask and treated with 0.3 mL trimethylsilyl chloride. A portion of HMDS (ca. 25 mL) was added, and an exothermic reaction took place as the mixture became homogeneous. The remainder of the HMDS (121 mL, 0.69 mol total) was added at a controlled rate (ca. 3–5 mL/min), maintaining the reaction temperature at ca. 60° C. Heating was continued at 100° C. (3 h), and 150° C. (1.5 h). Distillation provided 130.6 g of colorless oil, bp 80°–81° C./15 mm. GC analysis (method 1) showed ca. 99% purity.

EXPERIMENT 3

Preparation of $(CH_3)_3SiO(CH_2)_4OSi(CH_3)_3$ 1,4-Butanediol (54 g, 0.60 mol) was placed in a 500 mL 3-necked RB flask and treated with 0.3 mL trimethylsilyl chloride. A portion of HMDS (ca. 20 mL) was added, and an exothermic reaction took place as the mixture became homogeneous. The remainder of the HMDS (120 mL, 0.66 mol total) was added at a controlled rate (ca. 3–5 mL/min), maintaining the reaction temperature at ca. 50° C. Heating was continued at 100° C. (3 h), and 150° C. (1.5 h). GC analysis (method 1) revealed excess HMDS and one product. Distillation provided 127.8 g of colorless oil, bp 97°–99° C./15 mm. $^1H$ NMR (CDCl$_3$): 3.75–3.50 (m, 4H), 1.75–1.50 (m, 4H), 0.16 (s, 18H).

EXPERIMENT 4

Preparation of $(CH_3)_3SiO(CH_2)_5OSi(CH_3)_3$ 1,5-Pentanediol (65 g, 0.62 mol) was placed in a 500 mL 3-necked RB flask and treated with 0.4 mL trimethylsilyl chloride. A portion of HMDS (ca. 20 mL) was added, and an exothermic reaction took place as the mixture became homogeneous. The remainder of the HMDS (130 mL, 0.71 mol total) was added at a controlled rate (ca. 3–5 mL/min), maintaining the reaction temperature at ca. 50° C. Heating was continued at 100° C. (1 h), and 150° C. (2.5 h). GC analysis (method 1) revealed excess HMDS and one product. Distillation provided 139 g of colorless oil, bp 47°–49° C./0.1 mm. $^1H$ NMR (CDCl$_3$): 3.60 (t, J=7Hz, 4H), 1.57 (m, 4H), 1.40 (m, 2H), 0.12 (s, 18H), consistent with the assigned structure.

EXPERIMENT 5

Preparation of $(CH_3)_3SiOCH(CH_3)CH_2OSi(CH_3)_3$ 1,2-Propanediol (58.8 g, 0.77 mol) was placed in a 500 mL 3-necked RB flask and treated with 0.2 mL trimethylsilyl chloride. A small volume of HMDS (ca. 10 mL) was added, and an exothermic reaction took place as the mixture became homogeneous. The remainder of the HMDS (170 mL) was added at a controlled rate (ca. 3–5 mL/min), maintaining the reaction temperature at ca. 50°–70° C. Heating was continued at 100° C. (1.5 h), 120° C. (1.0 h),and 140° C. (2.5 h). GC analysis (method 1) revealed excess HMDS and one product. Distillation provided 147 g of colorless oil, bp 70°–72° C./10 mm. $^1H$ NMR (CDCl$_3$): 3.83 (m, 1H), 3.50 and 3.38 (AB pattern with additional coupling, 2H), 1.15 (d, J=7 Hz, 3H), 0.15 (partially resolved singlets, 18H).

EXPERIMENT 6

Preparation of $(CH_3)_3SiOCH_2(CF_2)_3CH_2OSi(CH_3)_3$

A sample of 2,2,3,3,4,4-hexafluoro-1,5-pentanediol (10.3 g, 48.6 mmol) was treated with trimethylsilyl chloride (0.1 mL) and HMDS (8.4 g, 52 mmol). The mixture was heated slowly to 80° C. for 2.0 h and was heated briefly (ca. 15 min.) at 125° C. Crude product was transferred from the reactor under vacuum and was redistilled to give 16.1 g of colorless oil (93% yield), bp 40° C./0.1 mm. GC analysis (method 1) showed >99.8% purity. $^{19}F$ NMR (CDCl$_3$/fluorotrichloromethane (F11): −122.4 (m, 4F), −126.4 (s, 2F). $^1H$ NMR (CDCl$_3$): 4.08 (m, 4H), 0.20 (s, 18H).

EXPERIMENT 7

Preparation of $(CH_3)_3SiOCH_2(CF_2)_2OCF(CF_3)CF_2OCF(CF_3)CH_2OSi(CH_3)_3$

A) Preparation of $CH_3OOC(CF_2)_2OCF(CF_3)CF_2OCF(CF_3)COOCH_3$

A mixture of sodium fluoride (12 g) and methanol (200 mL) was cooled to 0° C. and treated slowly with the diaduct ester $(CH_3OOC(CF_2)_2OCF(CF_3)CF_2OCF(CF_3)COF$, DAE) prepared from methyl difluoromalonyl fluoride and hexafluoropropylene oxide (HFPO)(116 g, 0.24 mol) as described in U.S. Pat. No. 4,138,426. The mixture was warmed to 25° C. and stirred for 3 h. Filtration and removal of solvent gave a residue which was distilled to provide 71.8 g, bp 96°–103° C./14 mm. GC analysis (method 1) showed two diastereomers with purity >99.8%. 19F NMR (CDCl$_3$/F11): −79.25 and −79.75 (low-field portions of AB patterns, $J_{AB}$=147 Hz, 1F), −85.75 and −86.30 (upfield portions of AB patterns, 1F), −80.5 (m, 3F), −82.8 (s, 3F), −83.5 (m, 2F), −121.7 (s, 2F), −132.2 (overlapping m's, ester end CF), −145.9 (apparent t, middle CF).

B) Preparation of $HOCH_2(CF_2)_2OCF(CF_3)CF_2OCF(CF_3)CH_2OH$

A solution of $CH_3OOC(CF_2)_2OCF(CF_3)CF_2OCF(CF_3)COOCH_3$ (68.5 g, 137 mmol) in methanol (300 mL) at 0° C. was treated in portions with sodium borohydride (10.3 g, 271 mmol). Temperature was controlled at 10°–20° C. After stirring for 16 h, most of the solvent was removed under vacuum. The residue was diluted with ether, washed with water, saturated sodium chloride, and dried (MgSO$_4$). Evaporation gave a residue which was kugelrohr distilled to give 56.3 g, bp 65°–72° C./ca. 0.1 mm. GC analysis (method 1) showed two diastereomers (58/42) in >99% purity. $^{19}F$ NMR (acetone-d$_6$ or THF-d$_8$): −78.2–−84.2 (multiplets, including AB patterns −82.7 and −83.7 (J=145), −78.8 and −80.8 (J~145), and −79.2 and −81.2 (J~145), −125.16 and −125.22 (triplets, $J_{HF}$=14 Hz, 2F), −145.16 and −145.28 (triplets, $J_{FF}$=22 Hz, 1F). $^1H$ NMR (acetone-d6): −5.31 (doubled triplets, $^3J_{HH}$=6.6 Hz), Δν$_{360}$ MHz=2.3 Hz for two diastereomers, (1 H), 5.12 (t, $^3J_{HH}$=6.8 Hz, 1H), 4.24 (dd, J=6, 12.7 Hz, 2H), 4.04 (t of doublets, $J_{HF}$=14.5, $J_{HH}$=6.0 Hz, 2H). Addition of a trace of HCl caused the disappearance of hydroxyl proton signals and simplification of the remaining signals to 4.22 (d, J=13) and 4.03 (t, J=14.4 Hz). $^1H$ NMR (THF-d$_8$): 5.32 (t, J=6.7 Hz, 1H), 5.13 and 5.12 (triplets, J=7 Hz, 1H), 4.11 (dd, J=6, 12.7 Hz, 2H), 3.93 (t of d, J=14.5, 6.0 Hz).

C) Preparation of $(CH_3)_3SiOCH_2(CF_2)_2OCF(CF_3)CF_2OCF(CF_3)CH_2OSi(CH_3)_3$ $HOCH_2(CF_2)_2OCF(CF_3)CF_2OCF(CF_3)CH_2OH$ (28.8 g, 64.9 mmol) was chilled in ice and treated with HMDS (26.5 g, 164 mmol). The mixture was warmed to 25° C. and stirred for 2.5 h. GC analysis (method 1) showed complete conversion to two diastereomeric products (retention time=11.59, 11.64 min) in >99.3% purity. $^{19}$F NMR (THF-d$_8$): −79.4 and −81.2 (AB pattern, J$_{AB}$=160 Hz, 2F), −79.8 (unresolved m, 3F), −81.9 and −82.0 (singlets, Δν$_{188.2MHz}$=13 Hz, 3F), −82.7 and −83 3 (AB pattern, J$_{AB}$=160 Hz), 124.6 (t, J=11 Hz) and −124.7 (t, J=14 Hz, combined 2F), −134.6 (m, 1F, CFCH$_2$), −145.04 (t, J=22 Hz) and −145.20 (t, J=22 Hz, combined 1F, internal CF). $^1$H NMR (THF-d$_8$): 4.20 (t, J=11.8 Hz, 2H), 4.05 (t, J=13.6 Hz) and 4.04 (t, J=13.6 Hz, 2H), 0.14 and 0.13, Δν$_{188.2MHz}$=3.2 Hz). Ratio of diastereomers was 50/50 within experimental error.

EXPERIMENT 8

Preparation of
(CH$_3$)$_3$SiOCH$_2$(CF$_2$)$_2$O[CF(CF$_3$)CF$_2$O]$_2$CF(CF$_3$)CH$_2$OSi(CH$_3$)$_3$ A) Preparation of
CH$_3$OOC(CF$_2$)$_2$O[CF(CF$_3$)CF$_2$O]$_2$CF(CF$_3$)COOCH$_3$

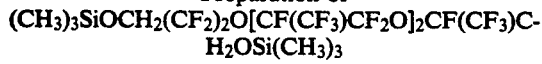

A mixture of sodium fluoride (12 g) and methanol (200 mL) was cooled to 0° C. and treated slowly with the triadduct ester CH$_3$OOC(CF$_2$)$_2$O[CF(CF$_3$)CF$_2$O]$_2$CF(CF$_3$)COF, (TAE) prepared from methyl difluoromalonyl fluoride and HFPO (136 g) as described in U.S. Pat. No. 4,138,426. The mixture was warmed to 25° C. and stirred for 18 h. Filtration and removal of solvent gave a residue which was distilled to provide 111 g, bp 55°–63° C./0.05 mm. GC analysis (method 1) showed four diastereomers with purity >98%. $^{19}$F NMR (acetone-d$_6$): −78 to −79.5 (low-field portion of AB pattern), −79.8 to −82.8 (m), −84.5 (upfield portion of AB pattern), −121.0 (m, 2F), −131.0 (overlapping m's, ester end CF), −144.9 (m). IR (thin film) 1790 cm$^{-1}$.

B) Preparation of
HOCH$_2$(CF$_2$)$_2$O[CF(CF$_3$)CF$_2$O]$_2$CF(CF$_3$)CH$_2$OH A solution of CH$_3$OOC(CF$_2$)$_2$O[CF(CF$_3$)CF$_2$O]$_2$CF(CF$_3$)COOCH$_3$ (21.5 g, 32.3 mmol) in methanol (100 mL) at 0° C. was treated in portions with sodium borohydride (2.6 g, 68 mmol). Temperature was controlled at 10°–20° C. After stirring for 16 h, most of the solvent was removed under vacuum. The residue was diluted with ether, washed with water, saturated sodium chloride, and dried (MgSO$_4$). Evaporation gave a residue which was kugelrohr distilled to give 17.6 g, bp 75° C./0.05 mm. GC analysis (method 1) showed a mixture of diastereomers in >97% purity. $^{19}$F NMR (acetone-d$_6$): −78.0 to −84.0 (multiplets, 15F), −125.1 (m, CH$_2$CF$_2$), −134.5 (m, terminal CF), −145.0 (m, internal CF).

C) Preparation of
(CH$_3$)$_3$SiOCH$_2$(CF$_2$)$_2$O[CF(CF$_3$)CF$_2$O]$_2$CF(CF$_3$)CH$_2$OSi(CH$_3$)$_3$ HOCH$_2$(CF$_2$)$_2$O[CF(CF$_3$)CF$_2$O]$_2$CF(CF$_3$)CH$_2$OH (17.6 g, 28.9 mmol) was chilled in ice and treated with HMDS (11.8 g, 73.3 mmol). The mixture was warmed to 25° C. and stirred for 1.0 h. GC analysis (method 1) showed complete conversion to diastereomeric products (retention time ca. 12.3 min). Excess HMDS was removed under vacuum at ca. 40° C. to provide 21 g of colorless oil. Kugelrohr distillation gave a sample with bp 65° C./0.05 mm. $^{19}$F NMR (CDCl$_3$): −79.6 to −84.05 (series of m, CF$_3$ and OCF$_2$), −125.6 (m, OCH$_2$CF$_2$), −135.8 (m, CH$_2$CF), −146.0 (m, internal CF), consistent with the assigned structure.

EXPERIMENT 9

Preparation of
p—(CH$_3$)$_3$SiOPhC(CF$_3$)$_2$PhOSi(CH$_3$)$_3$—p

Bisphenol AF (50 g, 0.15 mol) in 50 mL glyme was treated with HMDS (50 g, 0.3 mol). The mixture was heated slowly and then heated at reflux for 2.0 h. GC analysis (method 1) showed quantitative conversion to one product. Low-boiling materials were removed under vacuum, and product was kugelrohr distilled to provide 70 g of colorless oil which crystallized (mp 54°–56° C.). $^1$H NMR (THF-d$_8$): 7.25 and 6.85 (AB pattern, J$_{AB}$=8 Hz, 8H). 0.27 (s. 18 H).

EXAMPLE 1

Preparation of
CF$_3$(F)C=C(F)OCH$_2$(CF$_2$)$_2$OCF(CF$_3$)CF$_2$OCF(CF$_3$)CH$_2$OC(F)=C(F)CF$_3$

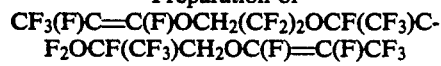

A solution of (CH$_3$)$_3$SiOCH$_2$(CF$_2$)$_2$OCF(CF$_3$)CF$_2$OCF(CF$_3$)CH$_2$OSi(CH$_3$)$_3$ (23.0 g, 39 mmol) in glyme (100 mL) at −60° C. was treated with hexafluoropropene (HFP) (16.8 g, 112 mmol) and cesium fluoride (1.3 g). The mixture was warmed slowly (2.0 h) to 0° C. and stirred at this temperature for 2.0 h. Excess HFP was removed under vacuum. The remaining mixture was diluted with ether, washed with ice water and sodium chloride solution, dried, and evaporated to provide 29.1 g of crude product. Kugelrohr distillation gave 14.7 g, bp 35°–47° C./0.1 mm. Spinning band distillation removed small amounts of lower-boiling materials and gave a center cut of title compound (5.4 g), bp 47°–48° C./0.05 mm. $^{19}$F NMR (THF-d$_8$): −67.7 (m, CF$_3$), −79 to −83.4 (m, CF$_3$ and OCF$_2$), −95.5 and −96.2 (m's, vinyl F at Cl trans to CF$_3$ groups), −111.5 (overlapping doublets of quartets, J$_d$=125 Hz, vinyl F on Cl cis to CF$_3$), −123.8 (m, CF$_2$CH$_2$), −134.5 to 135.5 (m, CFCH$_2$), −144.5 (m, central CF group), −184.0 (overlapping m, vinyl F on C$_2$ "Z"-ends), −189.92 and −190.22 (overlapping d of quartets, J$_d$=120 Hz, vinyl F on C$_2$, "E"-ends). $^1$H NMR (THF-d$_8$): −4.81 (t, J=12.9 Hz), 4.87 (t, J=12.7 Hz), 4.96 (d, J=11.4 Hz), 5.03 (d, J=11.5 Hz).

EXAMPLE 2

Preparation of
CF$_3$(F)C=C(F)OCH$_2$(CF$_2$)$_2$O[CF(CF$_3$)CF$_2$O]$_2$CF(CF$_3$)CH$_2$OC(F)=C(F)CF$_3$

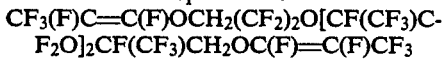

A solution of (CH$_3$)$_3$SiOCH$_2$(CF$_2$)$_2$O[CF(CF$_3$)CF$_2$O]$_2$CF(CF$_3$)CH$_2$OSi(CH$_3$)$_3$ (12.0 g, 15.9 mmol) in glyme (65 mL) at −60° C. was treated with HFP (6.8 g, 45.6 mmol) and cesium fluoride (0.5 g). The mixture was warmed slowly to 0° C. and stirred at this temperature for 2.5 h. The mixture was diluted with ether, washed with ice water and sodium chloride solution, dried, and evaporated to provide 14.5 g of crude product. GC analysis (method 1) showed four major isomers (65% of the mixture). Kugelrohr distillation gave 8.64 g, bp 70°–87° C. (0.1 mm). Spinning band distillation gave 5.4 g (bp 55°–58° C., 0.05 mm). IR: 1769 cm$^{-1}$ and 1250–1140 cm$^{-1}$ envelope $^{19}$F NMR (THF-d$_8$): −67.8 (m, CF$_3$), −78.5 to −83.3 (m, CF$_3$ and OCF$_2$), −95.6 (d of quartets, J$_q$=9.6 Hz, J$_d$=19.9 Hz, vinyl F on Cl trans to CF$_3$), −96.4 (d of quartets, J$_d$=9.6 Hz, J$_d$=19.9

Hz, vinyl F on C3 trans to CF3), −111.6 (d of quartets. $J_q$=23 Hz, $J_d$=120 Hz) and −111.8 (d of quartets. $J_q$=23 Hz. $J_d$=120 Hz. vinyl F on Cl cis to CF3), −123.6 (m, CF2CH2), −134.3 to −135.3 (m, CFCH2), −144.8 (m, central CF groups), −184.0 (overlapping m, vinyl F on C2 "Z"-ends), −190.2 (d of quartets, $J_d$=120 Hz, $J_q$=13.2 Hz) and −190.0 (d of quartets $J_q$=13 Hz, $J_q$=120 Hz, vinyl F on C2 "E"-ends). Ratio of J=12.8 Hz, major), 4.88 (t, J=12.6 Hz, minor), 4.97 (d, J=11.2 Hz, major), 5.04 (d, J=11.3 Hz, minor). E/Z ratio obtained from $^{19}$F NMR data. GC/MS (positive ion, EI) showed the major component with M+ of m/z=870 and (M-F)=851, consistent with bis(vinyl) ether isomers of the title structure.

EXAMPLE 3

Preparation of

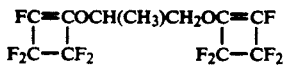

A solution of $(CH_3)_3SiOCH(CH_3)CH_2OSi(CH_3)_3$ (4.32 g, 19.6 mmol) and tris(piperidino)sulfonium trimethyldifluorosilicate (TPSF) (100 mg), prepared as described in U.S. Pat. No. 3,940,402, in THF (20 mL) was treated with perfluorocyclobutene (7.39 g, 45 mmol) while the temperature was controlled between 30° and 35° C. The mixture was stirred at ambient temperature for 24 h. The reaction mixture was diluted with ether, washed with ice water, dried (MgSO4), and evaporated to give 4.58 g of crude residue. Kugelrohr distillation (ca. 50° C., 0.1 mm) gave 3.72 g of oil. $^{19}$F NMR (CDCl3/F11) featured: −116.4 to −117.1 (m, 4F), −118.9 to −119.7 (m, 4F), −138.8 and −139.1 (equally intense m, 2F). GC/MS showed one major component with M+ of m/z=360.0297. Calcd for $C_{11}H_6F_{10}O_2$=360.0208. All these are consistent with the title compound.

EXAMPLE 4

Preparation of

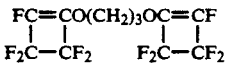

A solution of $(CH_3)_3SiO(CH_2)_3OSi(CH_3)_3$ (4.40 g, 20 mmol) and TPSF (100 mg in 1.0 mL THF) in THF (20 mL) was treated with perfluorocyclobutene (4.4 mL, 45 mmol) while the temperature was controlled between 30° and 35° C. The mixture was stirred at ambient temperature for 24 h. The reaction mixture was diluted with ether, washed with ice water, dried (MgSO4), and evaporated to give 6.68 g of light yello solid. GC analysis (method 1) showed one major component eluted at 10.3 min (92% purity). Kugelrohr distillation (ca. 50°-55° C., 0.1 mm) gave 5.60 g of white solid, mp 43°-45° C. $^{19}$F NMR (CDCl3/F11): −116.8 (m, 4F), −119.3 (m, 4F), −140.45 (m, 2F). GC/MS showed one major component with M+ of m/z=360.0225. Calcd for $C_{11}H_6F_{10}O_2$=360.0208. All these are consistent with the title compound.

EXAMPLE 5

Preparation of

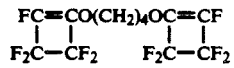

A solution of $(CH_3)_3SiO(CH_2)_4OSi(CH_3)_3$ (18.4 g, 78 mmol) and tris(dimethylamino)sulfonium difluorotrimethylsilicate (TASF) (100 mg), prepared as described in U.S. Pat. No. 3,940,402, in THF (65 mL) was treated with perfluorocyclobutene (18.5 mL, 180 mmol) while the temperature was controlled between 25° and 30° C. Another 100 mg TASF was added, and the mixture was stirred at ambient temperature for 24 h. The reaction mixture was diluted with ether, washed with ice water, dried (MgSO4), and evaporated and Kugelrohr distilled to give 24.98 g of colorless oil. GC analysis (method 1) showed one major component (retention time=11.3 min), purity 94.5%. Spinning band distillation (70° C./0.05 mm) gave a sample with purity >98.6%. $^{19}$F NMR (CDCl3/F11): −116.65 (m, 4F), −119.5 (m, 4F), 141.40 (m, 2F). $^1$H NMR (CDCl3): 4.30 (m, 4H), 1.92 (m, 4H). GC/MS (positive ion, EI) showed one component with highest observed mass of m/z=355.0463. Calcd for $C_{12}H_8F_9O_2$=355.0380 (corresponding to M-F). Anal. Calcd for $C_{12}H_6F_{10}O_2$: C, 38.52; H, 2.16; F, 50.77. Found: C, 38.51; H, 2.31; F, 48.25. All these are consistent with the title compound.

EXAMPLE 6

Preparation of

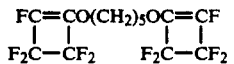

A solution of $(CH_3)_3SiO(CH_2)_5OSi(CH_3)_3$ (4.96 g, 20 mmol) and TPSF (100 mg in 0.5 mL THF) in glyme (25 mL) at 0° C. was treated with perfluorocyclobutene (7.13 g, 44 mmol). The mixture was stirred at ambient temperature for 24 h. The reaction mixture was diluted with ether (200 mL), washed with ice water, saturated NaCl soln., dried (MgSO4), and evaporated to give an oil which was fractionally kugelrohr distilled. The major fraction, 4.77 g, bp 87° C. at 0.1 mm, consisted of one major component (ca. 75%). $^{19}$F NMR (CDCl3/F11): −116.5 (d, 4F), −119.4 (m, 4F), −141.5 (m, 2F). GC/MS (positive ion, EI) showed one major component with M+ of m/z=388, corresponding to the desired 2/1 adduct (title compound) $(C_{13}H_{10}F_{10}O_2)$.

EXAMPLE 7

Preparation of

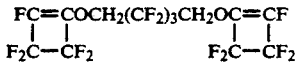

A solution of $(CH_3)_3SiOCH_2(CF_2)_3CH_2OSi(CH_3)_3$ (17.8 g, 49.9 mmol) in glyme (125 mL) at −50° C. was treated with perfluorocyclobutene (32.3 g, 200 mmol) and cesium fluoride (0.5 g). The mixture was warmed to 0° C. and stirred for 2.5 h. It was then allowed to warm slowly to 25° C. over 18 h. The mixture was diluted with ether, washed with water, dried, evaporated, and kugelrohr distilled to give 21.8 (88% yield) colorless oil, bp 60° C. (0.1 mm). GC analysis (method 1) showed 99.6% purity. $^{19}$F NMR (THF-d$_8$): −117.15 (m, 4F), −119.8 (m, 4F), 120.7 (m, 4F), −125.3 (s, 2F), −138.55 (m, 2F(vinyl)). $^1$H NMR (THF-d$_8$): 5.00 (m). All these are consistent with the title compound.

EXAMPLE 8

Preparation of

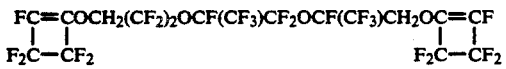

A solution of (CH$_3$)$_3$SiOCH$_2$(CF$_2$)$_2$OCF(CF$_3$)CF$_2$OCF(CF$_3$)CH$_2$OSi(CH$_3$)$_3$ (17.0 g, 28.9 mmol) in glyme (75 mL) was treated with perfluorocyclobutene (20.7 g, 128 mmol) at −40° C. CsF (0.5 g) was added, and the mixture was warmed slowly to 0° C. The mixture was stirred for 2.5 h at 0° C., then for 18 h at 25° C. Excess perfluorocyclobutene and trimethylsilylfluoride (TMSF) were removed under vacuum. The remainder was diluted with ether, washed with water, dried and stripped to give 21.9 g of crude product which was kugelrohr distilled to provide 19.2 g (82.4%) (bp 80°–90° C./ca. 0.1 mm). IR: 1766 cm$^{-1}$ (C═C), 1373, 1241, and 1138 cm$^{-1}$. $^{19}$F NMR (THF-d$_8$): −79.77 and −80.85 (AB pattern, J$_{AB}$=150 Hz, 2F), −80.0 (s, 3F), −82.5 (s, 3F), 83.2 (m, 2F), −117.3 (m, 1F), −120.0 (m, 4F). −123.7 (t, J=12.4 Hz, 2F), −135.6 (m, 1F), −138.0 (m, 1F), −138.6 (m, 1F), 144.8 (apparent t, J=22 Hz, 1F). $^1$H NMR (THF-d$_8$): 5.13 (d, J=12.4 Hz, 2H), 5.00 (t, J=12.6 Hz, 2H). GC/MS showed two components, each with M$^+$ of m/z=728. Also observed was M-F with m/z=709.

EXAMPLE 9

Preparation of

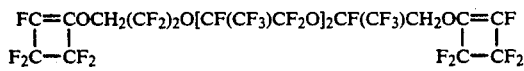

A solution of (CH$_3$)$_3$SiOCH$_2$(CF$_2$)$_2$O[CF(CF$_3$)CF$_2$O]$_2$CF(CF$_3$)CH$_2$OSi(CH$_3$)$_3$ (6.73 g, 8.93 mmol) in glyme (30 mL) was treated with perfluorocyclobutene (17.3 g, 107 mmol) at −55° C. TPSF (100 mg) was added, and the mixture was warmed slowly to 25° C. Excess perfluorocyclobutene and TMSF were removed under vacuum. The remainder was stripped and kugelrohr distilled to give 7.39 g of colorless oil (bp 80°–85° C./0.05 mm, 92% purity, 85% yield). Spinning band distillation gave 5.91 g (bp 73°–81° C., 0.05 mm). IR: 1766 cm$^{-1}$ (C═C). $^{19}$F NMR (THF-d$_8$): −78.7 to −83.2 (m's, 15 F), −117.2 (m, 4F), −119.9 (m, 4F), −123.7 (t, J=12.5 Hz, 2F), −135.6 (m, 1F), −138.0 (m, 1F), −138.7 (m, 1F), −145.0 (m, 2F). $^1$H NMR (CDCl$_3$): 4.75 (d, J=10.9 Hz, 2H), 4.62 (t, J=11.9 Hz, 2H). GC/MS showed a major component which exhibited a high mass fragment m/z=825, consistent with M-(CF$_3$). All these are consistent with the title compound.

EXAMPLE 10

Preparation of

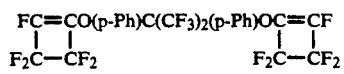

A solution of (CH$_3$)$_3$SiO(p—Ph)C(CF$_3$)$_2$(p—Ph)OSi(CH$_3$)$_3$ (14.4 g, 30 mmol) in glyme (50 mL) at 0° C. was treated with TPSF (100 mg in 1.0 mL glyme). Perfluorocyclobutene (11.3 g, 70 mmol) was added to the resulting solution at 0°–7° C. (ca. 10 min.). After addition was complete more TPSF (50 mg in 0.5 mL glyme) was added and the reaction mixture warmed to 25° C. After 3.0 h at this temperature, volatiles were removed under vacuum. The material was taken up in 1,1,2-trifluoro-1,2,2-trichloroethane (F$_{113}$), washed with water, dried, and stripped to give 19.2 g of residue. Recrystallization from petroleum ether at −5° C. gave 12.7 g, mp 49°–51° C. $^{19}$F NMR (CDCl$_3$/F11): −64.46 (s, 6F), −117.5 (m, 4F), −118.9 (m, 4F), and −129.35 (m, 2F). $^1$H NMR (CDCl$_3$): 7.32 and 7.10 (aryl AA'BB'). All these are consistent with the title compound.

EXAMPLE 11

Preparation of

CF$_3$(F)C═C(CF$_3$)OCH$_2$(CF$_2$)$_2$OCF(CF$_3$)CF$_2$OCF(CF$_3$)CH$_2$OC(CF$_3$)═C(F)CF$_3$

A solution of (CH$_3$)$_3$SiOCH$_2$(CF$_2$)$_2$OCF(CF$_3$)CF$_2$OCF(CF$_3$)CH$_2$OSi(CH$_3$)$_3$ (2.86 g, 4.86 mmol) in glyme (25 mL) at −50° C. was treated with perfluoro-2-butene (3.2 g, 16 mmol) and cesium fluoride (0.4 g). The mixture was warmed to 0° C. and stirred for 1.0 h. GC analysis (method 1) showed: one component at 5.9 min (12%), a group of six resolved components at 7.8–8.3 min (49%), and a third group of components at 12.3–12.9 min (19%). The mixture was diluted with ether, filtered, and evaporated to give 4.3 g of crude residue. Fractional kugelrohr distillation (0.1 mm) gave 0.6 g with bp ca. 25°–30° C. The $^{19}$F NMR spectrum (THF-d$_8$) of this portion featured: −62.53 (q, J=11.4 Hz, —CF$_3$), −64.37 (q, J=11.4 Hz, —CF$_3$), −63.0 (m, —CF$_3$), −65.5 (m, —CF$_3$), −76.0 to −88.3 (m, —CF$_3$+—OCF$_2$—), −121.0 and −125.2 (AB pattern, J$_{AB}$=285 Hz, CF$_2$), −121.8 and −124.7 (AB pattern, J=285 Hz) −136.6 (m, CF), −139.6 (m, CF), −147.65 and −149.6 (m's, internal CF groups). GC/MS exhibited M$^+$ of m/z=604. These data are consistent only with diastereomeric 1/1 cyclic adducts. The next highest boiling fraction (1.5 g), collected at 55°–100° C., consisted of cyclic 1/1 adducts (18%) and isomeric bis(vinyl) ethers of the above structure. $^{19}$F NMR (THF-d$_8$) featured: −65.6 and −68.45 (m, —CF$_3$), −79.3 to −81.0 and −82.0 to −83.4 (m, CF$_3$ and OCF$_2$), −123.55 and −124.0 (m, CF$_2$CH$_2$), −134.8 and −135.4 (m, CFCH$_2$), −138.0, −138.2, −142.6, and −143.8 (m's, vinyl F), −144.75 (m, central CF). $^1$H NMR 4.96 (d, J=10.5 Hz), 4.80 (t, J=12.5), 4.69 (d, J=11 Hz), 4.57 (t, J=12.4 Hz). IR: 1698 cm$^{-1}$ (C═C) and large absorption band 1285 to 1160 cm$^{-1}$. GC/MS showed a major group of isomers, each with M$^+$ of m/z=804, consistent with the assigned 2/1 (title) adduct structures.

EXAMPLE 12

Preparation of

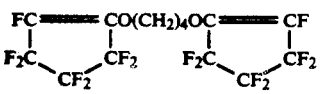

A solution of $(CH_3)_3SiO(CH_2)_4OSi(CH_3)_3$ (7.73 g, 33 mmol) and TPSF (50 mg in 0.5 mL THF) in THF (20 mL) was treated with perfluorocyclopentene (14.8 g, 70 mmol) using a small stainless steel canula. Another 100 mg TPSF in 1.0 mL THF was added, and the mixture was stirred at ambient temperature for 24 h. The reaction mixture was diluted with ether, washed with ice water, dried ($MgSO_4$), and evaporated to give 15.55 g, mp 65°–68° C. (>99%). Sublimation (45°–50° C. at 0.1 mm) gave a sample with mp 67°–70° C. GC analysis (method 1) showed one component (retention time=11.8 min). $^{19}F$ NMR ($CDCl_3/F11$): −115.4 (d, J=12.7 Hz, 4F), −116.67 (d, J=10.6 Hz, 4F), −130.1 (s, 4F), −162.4 (m, 2F). Anal. Calcd for $C_{14}F_{14}H_8O_2$: C, 35.46; H, 1.70; F, 56.09. Found: C, 34.48; H, 1.75; F, 57.56. GC/MS (positive ion, EI) showed one component with highest observed mass of m/z=265.0516. Calcd for $C_9H_8F_7O$-265.0463. This corresponds to M-($C_5F_7O$). All these are consistent with the title structure.

EXAMPLE 13

Preparation of
$(CF_3)_2C=C(CF_2CF_3)OCH_2(CF_2)_2OCF(CF_3)CF_2OCF(CF_3)CH_2C(CF_2CF_3)_2$ A mixture of $(CH_3)_3SiOCH_2(CF_2)_2OCF(CF_3)CF_2OCF(CF_3)CH_2OSi(CH_3)_3$ (4.12 g, 7.0 mmol) perfluoro-2-methyl-2-pentene (12.6 g, 42 mmol), and glyme (20 mL) at 0° C. was treated with cesium fluoride (75 mg) and stirred for 1.5 h. The mixture was warmed to 25° C. and stirred for 4.0 h. The mixture was distilled to provide 5.59 g of a colorless oil, bp 75° C./0.05 mm. IR featured 1644 cm$^{-1}$ (C=C). $^1H$ NMR (THF-$d_8$): 4.95 (d, J=13.7), 4.90 (t, J=12.4 Hz). $^{19}F$ NMR (THF-$d_8$) −56.3 (m, 6F), −59.1 (m, 6F), −78.5 to −83.4 (m's, including $CF_3$ signals at −80.0, −80.9, −81.1, and −82.2, $CF_2O$ m at −83.2, and AB pattern, $J_{AB}=140$ Hz, at −79.2/−80.9, total of 16 F), −113.0 (m, 4F), −123.5 (s, 2F), −136.5 (m, 1F), and −144.6 (m, 1F). GC analysis (method 1) showed two diastereomers with retention time ca. 9.5 min. GC/MS showed the parent ion with M$^+$ of m/z=1003.918. Calcd for $C_{21}H_4F_{36}O_4=1004.206$. All these are consistent with the title structure.

EXAMPLE 14

Preparation of Macrocyclic Compounds

A solution of $*C_4F_5OCH_2(CF_2)_2OCF(CF_3)CF_2OCF(CF_3)CH_2OC_4F_5$ (3.64 g, 5.0 mmol) ($*C_4F_5$ is perfluoro-1-cyclobutenyl) in glyme (175 mL) was treated with cesium fluoride (100 mg). A sample of $(CH_3)_3SiOCH_2(CF_2)_2OCF(CF_3)CF_2OCF(CF_3)CH_2OSi(CH_3)_3$ (2.66 g, 4.52 mmol) was added over a 1.0 h period. After 18 h at 25° C., the mixture was diluted with ether (50 mL), filtered, and evaporated to give 5.71 g of residue. Fractional kugelrohr distillation gave 2.30 g, bp 110°–130° C./0.05 mm. This portion was refractionated to give 1.54 g, bp 110°–120° C./0.05 mm. IR featured a band at 1752 cm$^{-1}$ (—C=C—) at 1365, 1308, 1238, 1171, 1112, 1071, and 1023 cm$^{-1}$. $^{19}F$ NMR (THF-$d_8$): −79.0 to −83.5 (m's, $CF_3$, $OCF_2$), −114.5 (m, a=48), −124.0 (m, $CF_2CH_2$), −135.0 (m, $CFCH_2$), −144.7 (m, central CF). $^1H$ NMR: 4.93 (d, J=10.7 Hz), 4.79 (t, J=12.5 Hz). Mass spectral analysis showed a large parent ion with nominal m/z=1132, as expected for the cyclic dimers ($C_{26}H_8F_{36}O_8$) of the formulas:

and

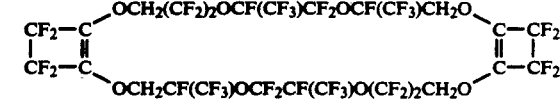

A sample was further purified by preparative HPLC on Zorbax4/4 silica, eluting with 95/5 hexane/methyl t-butyl ether. Small amounts of impurities were thereby removed, and the central cut was homogeneous as judged by GC analysis (method 1, retention time=13.94 min).

The pot residue was subjected to kugelrohr distillation and provided a higher-boiling fraction (200°–220° C.), 0.68 g. Mass spectral analysis showed a substantial parent ion m/z=2264, consistent with a cyclic tetramer of the repeat unit

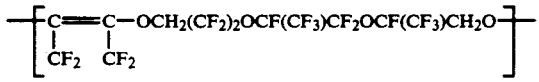

To examine the role of catalyst in the cyclization process, the reaction was repeated, using equimolar quantities of $C_4F_5OCH_2(CF_2)_2OCF(CF_3)CF_2OCF(CF_3)CH_2)OC_4F_5$ and $(CH_3)_3SiOCH_2(CF_2)_2OCF(CF_3)CF_2OCF(CF_3)CH_2)OSi(CH_3)_3$ (5.0 mmol) in 100 mL glyme solution to which was added catalyst, either cesium fluoride (150 mg) or TASF (68 mg). Work-up, as above, gave: from the TASF reaction, 1.00 g 80% purity), and from the CsF reaction, 1.59 g (88% purity).

EXAMPLE 15

Polymerization of $(CH_3)_3SiOCH_2(CF_2)_2OCF(CF_3)CF_2OCF(CF_3)CH_2OSi(CH_3)_3$ with Hexafluoropropene A weighed sample of hexafluoropropene (2.06 g, 13.7 mmol) was added to glyme (30 mL) at −50° C. $(CH_3)_3SiOCH_2(CF_2)_2OCF(CF_3)CF_2OCF(CF_3)CH_2OSi(CH_3)_3$ (8.08 g. 13.7 mmol) and cesium fluoride (150 mg) were added, and the mixture was warmed slowly to −10° C. After 0.5 h at −10° C., the mixture was maintained at 0° C. for 2.0 h, then allowed to warm slowly to 20° C. for 16 h. The supernatant was decanted, and solids were washed with glyme to provide 2.99 g of rubbery solid and 4.10 g of soluble residue after evaporation. IR (soluble fraction): 1732 cm$^{-1}$ (C=C). Lower-boiling components were removed by kugelrohr distillation (up to 130° C. @0.05 mm) to give 3.0 g of residue. $^{19}F$ NMR (THF-$d_8$): −67.0 (m, a=25), −78.5 to −84.0 (m's, a=124), −124.0 (m, a=47), −135 (m, a=21), −145 (m, a=21), −178.7 to −181 (m's, a=7). Integration values for vinyl CF and CF3 and C=C signals were low. Size exclusion chromatography showed $M_n$=4900 for the major fraction of material. The data are consistent with a polymer of the structure

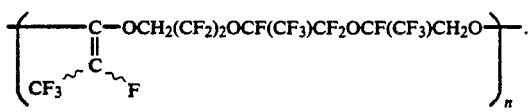

EXAMPLE 16

Polymerization of

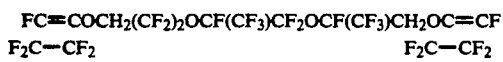

with
(CH3)3SiOCH2(CF2)2OCF(CF3)CF2OCF(CF3)C-H2OSi(CH3)3 in Tetrahydrofuran (High Temperature)

A mixture of C4F5OCH2(CF2)2OCF(CF3)C-F2OCF(CF3)CH2OC4F5 (2.72 g, 3.74 mmol) and (CH3)3SiOCH2(CF2)2OCF(CF3)CF2OCF(CF3)C-H2OSi(CH3)3, (2.45 g, 4.16 mmol) in THF (20 mL) at reflux was treated with TASF (30 mg in 1 mL THF). Heating of the mixture at reflux was continued for 15 min. An aliquot was removed and analyzed by $^{19}$F NMR and size exclusion chromatography. $^{19}$F NMR (THF-d8): −78.8 to −83.5 (m's, a=73), −114.8 (s, a=18), −117.2 (m, a=3) and −119.8 (m, a=3), −123.8 and −124.2 (m's, combined a=12), −138.0 and −138.6 (m, a=1.5), −144.8 (m, a=12.5). Ratio of internal ring CF2 signal to terminal ring CF2 signal=3.0/1. Size exclusion chromatography showed the bulk of sample with $M_n$=3000, $M_w$=3800.

The data are consistent with a polymer of the structure

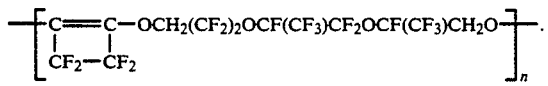

EXAMPLE 17

Polymerization of

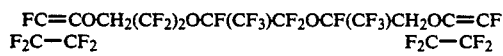

with
(CH3)3SiOCH2(CF2)2OCF(CF3)CF2OCF(CF3)C-H2OSi(CH3)3 in Tetrahydrofuran with TAS Camphorsulfinate Catalyst A solution of C4F5OCH2(CF2)2OCF(CF3)C-F2OCF(CF3)CH2OC4F5 (147 mg, 0.25 mmol) and (CH3)3SiOCH2(CF2)2OCF(CF3)CF2OCF(CF3)C-H2OSi(CH3)3, (182 mg, 0.25 mmol) in THF-d8 (0.8 mL) was treated with TAS d-10-camphorsulfinate (30 mg). $^{19}$F NMR (THF-d8): −78.5 to −83.5 (m's, a=73), −114.8 (s, a=22), −117.2 (m, a=2.7) and −119.8 (m, a=2.7), −124.0 (m's, combined a=15), −135.5 (m, a=7), −144.8 (m, a=7) −157.2 (10 line multiplet for Me3SiF, a=5). Ratio of internal ring CF2 signal to terminal ring CF2 signal=4.1/1.

The data are consistent with a polymer of the structure

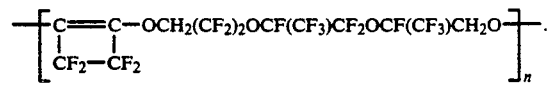

EXAMPLE 18

Polymerization of

with
(CH3)3SiOCH2(CF2)2OCF(CF3)CF2OCF(CF3)C-H2OSi(CH3)3

A mixture of C4F5OCH2(CF2)2OCF(CF3)C-F2OCF(CF3)CH2OC4F5 (5.1049 g, 7.01 mmol) and (CH3)3SiOCH2(CF2)2OCF(CF3)CF2OCF(CF3)C-H2OSi(CH3)3, (4.123 g, 7.01 mmol) was treated with TASF (50 mg). The temperature rapidly increased from 22° to 49° C., and TMSF was evolved rapidly. After the exotherm subsided (ca. 1 h), the mixture was heated at 65° C. for 1.25 h. After standing at room temperature for 48 h, another portion of catalyst (20 mg) was added and the mixture was heated at 70° C. for 1.0 h. $^{19}$F NMR (THF-d8): −79.8 and −81.3 (AB pattern, $J_{AB}$=145 Hz (CF2), a=21), −80.0 (s, a=31) and −82.5 (s, a=31, —CF3 groups), −83.2 (brd s, a=21, CF2), −114.9 (s, a−36, ring CF2 groups), −117.2 (m, a=2) and −119.8 (m, a=2, terminal ring CF2), −123.7 and −124.3 (s, combined a=21), −135.5 (m, a=9), −138.6 (m, a=1, terminal vinyl-F), −145.0 (m, a=10). Estimated $\overline{M}_n$=13,700 from integrated intensities. $^1$H NMR: trace signals at 5.17 (d) and 5.02 (t), 4.95 (d) and 4.80 (t, combined a=51), 4.5 to 4.4 (brd m, a=2). Size exclusion chromatography showed the bulk of product with $\overline{M}_n$=17,400, $\overline{M}_w$=24,900, in reasonable agreement with NMR estimate. The data are consistent with a polymer of the structure

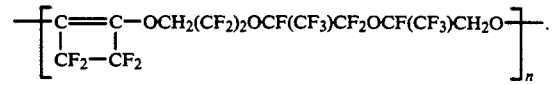

A small amount of cyclic dimer C26H8F36O8 (14%) was also produced.

EXAMPLE 19

Polymerization of

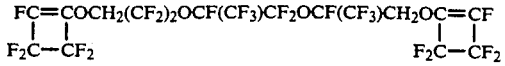

with
(CH$_3$)$_3$SiOCH$_2$(CF$_2$)$_2$OCF(CF$_3$)CF$_2$OCF(CF$_3$)CH$_2$OSi(CH$_3$)$_3$ A mixture of C$_4$F$_5$OCH$_2$(CF$_2$)$_2$OCF(CF$_3$)CF$_2$OCF(CF$_3$)CH$_2$OC$_4$F$_5$ (3.2650 g, 4.484 mmol) and (CH$_3$)$_3$SiOCH$_2$(CF$_2$)$_2$OCF(CF$_3$)CF$_2$OCF(CF$_3$)CH$_2$OSi(CH$_3$)$_3$, (2.639 g, 4.484 mmol) was treated with TPS benzoate (40 mg) prepared by the addition of trimethylsilyl benzoate to TPSF in THF following the general procedure described in U.S. Pat. No. 4,588,795. The temperature increased gradually to 49° C., and TMSF was evolved. After the exotherm subsided, the mixture was heated at 25° C. for 4 h. $^{19}$F NMR (THF-d$_8$): −79.8 and −81.3 (AB pattern, J$_{AB}$=145 Hz (CF$_2$)), −80.0 (s) and −82.5 (s), −83.2 (brd s), combined a=128, −114.9 (s, a-45), −117.2 (m, a=1) and −119.8 (m, a=1), −124.0 (m, a=25), −135.5 (m, a=12), −144.5 (m, a=12). $^1$H NMR: 4.90 (d) and 4.75 (t). Size exclusion chromatography showed the bulk of product with $\overline{M}_n$=10,400. The data are consistent with a polymer of the structure

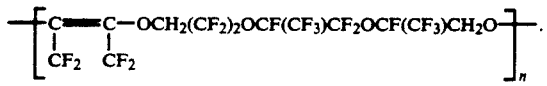

EXAMPLE 20

Polymerization of

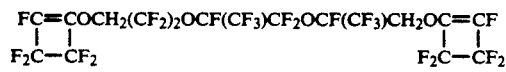

with
(CH$_3$)$_3$SiOCH$_2$(CF$_2$)$_2$OCF(CF$_3$)CF$_2$OCF(CF$_3$C-H$_2$OSi(CH$_3$)$_3$ in Trifluorotoluene A mixture of C$_4$F$_5$OCH$_2$(CF$_2$)$_2$OCF(CF$_3$)CF$_2$OCF(CF$_3$)CH$_2$OC$_4$F$_5$ (3.1468 g, 4.32 mmol) and (CH$_3$)$_3$SiOCH$_2$(CF$_2$)$_2$OCF(CF$_3$)CF$_3$)CF$_2$OCF(CF$_3$)CH$_2$OSi(CH$_3$)$_3$, (2.543 g, 4.32 mmol) in trifluorotoluene (13 mL) was treated with TASF (30 mg, 0.11 mmol). The temperature increased to 30° C. After the exotherm subsided, the mixture was stirred for 0.75 h. A 0.8 mL aliquot was removed, evaporated, and analyzed by $^{19}$F NMR and size exclusion chromatography. $^{19}$F NMR (THF-d$_8$): −79.0 to −83.5 (m=s, a=78), −114.9 (s, a=23), −117.2 (m, a=2.4) and −119.8 (m, a=2.4), −123.8 and −124.2 (m=s, combined a=14), −134.5 to −135.8 (m, a=7.5), −138.0 and −138.7 (m, a=1), −114.8 (m, a=7.3). Ratio of internal ring CF$_2$ signal to terminal ring CF$_2$ signal=4.8/1. Size exclusion chromatography showed the bulk of sample with $\overline{M}_n$=7400, $\overline{M}_w$=8500. The data are consistent with a polymer of the structure

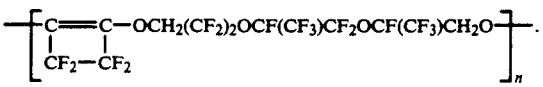

A 0.11 g sample of (CH$_3$)$_3$SiOCH$_2$(CF$_2$)$_2$OCF(CF$_3$)CF$_2$OCF(CF$_3$)CH$_2$OSi(CH$_3$)$_3$ was added, and the mixture was heated at 40° C. for 15 min and allowed to stand at 24° C. for 18 h. $^{19}$F NMR analysis showed the ratio of internal ring CF$_2$ signal to terminal ring CF$_2$ signal=6.6/1. Size exclusion showed $\overline{M}_n$=7700, $\overline{M}_w$=9500.

Another 0.13 g of sample of (CH$_3$)$_3$SiOCH$_2$(CF$_2$)$_2$OCF(CF$_3$)CF$_2$OCF(CF$_3$)CH$_2$OSi(CH$_3$)$_3$ was added, along with 15 mg TASF, and the mixture was heated at 40° C. for 0.5 h. $^{19}$F NMR showed the above mentioned ratio=11.8/1. Size exclusion chromatography showed $\overline{M}_n$=9800, $\overline{M}_w$=11,400. The presence of ca. 10%. cyclic dimer C$_{26}$H$_6$F$_{36}$O$_4$ leads to a systematic overestimate of $\overline{M}_n$ when using $^{19}$F NMR integration.

EXAMPLE 21

Polymerization of

with
(CH$_3$)$_3$SiOCH$_2$(CF$_2$)$_2$OCF(CF$_3$)CF$_2$OCF(CF$_3$)CH$_2$OSi(CH$_3$)$_3$ in Trifluorotoluene (High Temperature)

A mixture of C$_4$F$_5$OCH$_2$(CF$_2$)$_2$OCF(CF$_3$)CF$_2$OCF(CF$_3$)CH$_2$OC$_4$F$_5$ (3.152 g, 4.33 mmol) and (CH$_3$)$_3$SiOCH$_2$(CF$_2$)$_2$OCF(CF$_3$)CF$_2$OCF(CF$_3$)CH$_2$OSi(CH$_3$)$_3$, (2.547 g, 4.33 mmol) in trifluorotoluene (15 mL) at 70° C. was treated with TPSF (30 mg, 0.076 mmol). The temperature increased rapidly to 77° C. After the exotherm subsided, the mixture was stirred for 0.5 h. A 0.8 mL aliquot was removed, evaporated, and analyzed by $^{19}$F NMR and size exclusion chromatography. $^{19}$F NMR (THF-d$_8$): −79.0 and −83.5 (m's, a=116), −114.9 (s, a=34), −117.2 (m., a=4) and −119.8 (m, a=4), −123.8 and −124.2 (m's, combined a=22), −134.5 to −136.0 (m, a=120), −138.0 and −138.7 (m, a=2), −144.8 (m, a=12). Ratio of internal ring CF$_2$ signal to terminal ring CF$_2$ signal=4.3/1. The data are consistent with a polymer of the structure

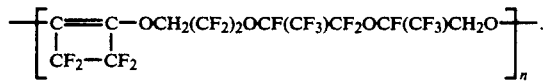

Size exclusion chromatography showed the bulk of sample with $\overline{M}_n$=5700, $\overline{M}_w$=6700.

A 0.25 g sample of (CH$_3$)$_3$SiOCH$_2$(CF$_2$)$_2$OCF(CF$_3$)CF$_2$OCF(CF$_3$)CH$_2$OSi(CH$_3$)$_3$ and 30 mg catalyst were added, and the mixture was heated at 80° C. for 1.0 h and at 90° C. for 2 h. $^{19}$F NMR analysis showed the ratio of internal ring CF$_2$ signal to terminal ring CF$_2$ signal=19/1. Size exclusion showed $\overline{M}_n$32 5100, $\overline{M}_w$=7400, Another 0.20 g sample of (CH$_3$)$_3$SiOCH$_2$(CF$_2$)$_2$OCF(CF$_3$)CF$_2$OCF(CF$_3$)CH$_2$OSi(CH$_3$)$_3$ was added, along with 25 mg TPSF, and the mixture was heated at 100° C. for 1.5 h. $^{19}$F NMR analysis showed only trace signals for olefinic end groups. Size exclusion chromatography showed $\overline{M}_n$=7700, $\overline{M}_w$=11,100. The presence of ca. 10% cyclic dimer leads to a systematic overestimate of $\overline{M}_n$ when using $^{19}$F NMR integration values.

EXAMPLE 22

Polymerization of

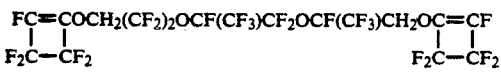

with
$(CH_3)_3SiOCH_2(CF_2)_2OCF(CF_3)CF_2OCF(CF_3)CH_2OSi(CH_3)_3$ in Trifluorotoluene (High Temperature)

A mixture of $C_4F_5OCH_2(CF_2)_2OCF(CF_3)CF_2OCF(CF_3)CH_2OC_4F_5$ (4.0895 g, 5.616 mmol) in trifluorotoluene (15 mL) was treated with TPSF (30 mg. 0.076 mmol) and heated rapidly to 50° C. $(CH_3)_3SiOCH_2(CF_2)_2OCF(CF_3)CF_2OCF(CF_3)CH_2OSi(CH_3)_3$, (3.367 g, 5.722 mmol) was added over a 5 min period by syringe, and the mixture was heated at 50° C. for 1.0 h. A 0.8 mL aliquot was removed, evaporated, and analyzed by $^{19}F$ NMR and size exclusion chromatography. $^{19}F$ NMR (THF-$d_8$): −79.0 and −83.5 (m's), a=137), −114.8 (S, a=46), −117.2 (m., a=2) and −119.8 (m, a=2), −124.2 (m, a=27), −135.0 (m, a=14), −145.0 (m, a=14). Ratio of internal ring $CF_2$ signal to terminal ring $CF_2$ signal=11.5/1. Size exclusion chromatography showed the bulk of sample with $\overline{M}_n=7100$, $\overline{M}_w=9800$. The data are consistent with a polymer of the structure

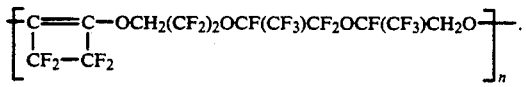

A 0.2 g sample of $(CH_3)_3SiOCH_2(CF_2)_2OCF(CF_3)CF_2OCF(CF_3)CH_2OSi(CH_3)_3$ and 20 mg catalyst was added, and the mixture was heated at 40° C. for 2.0 h. $^{19}F$ NMR analysis showed the ratio of internal ring $CF_2$ signal to terminal ring $CF_2$ signal=30/1. Size exclusion showed $\overline{M}_n=10,200$, $\overline{M}_w=13,000$.

EXAMPLE 23

Polymerization of

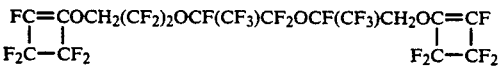

with
$(CH_3)_3SiOCH_2(CF_2)_2OCF(CF_3)CF_2OCF(CF_3)CH_2OSi(CH_3)_3$ in Tetrahydrofuran A mixture of $C_4F_5OCH_2(CF_2)_2OCF(CF_3)CF_2OCF(CF_3CH_2OC_4F_5$ (2.980 g, 4.092 mmol) and $(CH_3)_3SiOCH_2(CF_2)_2OCF(CF_3)CF_2OCF(CF_3)CH_2OSi(CH_3)_3$ (2.408 g, 4.092 mmol) in THF (13 mL) was treated with TASF (27 mg, 2.5 mol %). The temperature increased to 30° C. After the exotherm subsided, the mixture was stirred for 18 h at room temperature. An aliquot was removed and analyzed to $^{19}F$ NMR and size exclusion chromatography. $^{19}F$ NMR (THF-$d_8$): −79.0 to −83.5 (m's, a=130), −114.8 (s, a=35), −117.2 (m., a=5.5) and −119.8 (m, a=5.5), −123.7 and −124.2 (m's, combined a=23), −135.5 (m, a=12.5), −138.0 and −138.6 (m,=2.5), −144.8 (m, a=12.5). Ratio of internal ring $CF_2$ signal to terminal ring $CF_2$ signal=3.18/1. Size exclusion chromatography showed the bulk of sample with $\overline{M}_n=4200$, $\overline{M}_w=5400$. The data are consistent with a polymer of the structure

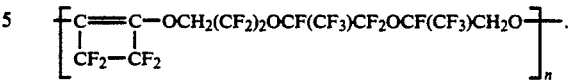

A second addition of $(CH_3)_3SiOCH_2(CF_2)_2OCF(CF_3)CF_2OCF(CF_3)CH_2OSi(CH_3)_3$ (0.28 g) and catalyst (20 mg) was made, followed by a 1.0 h period at 45° C. A third sample of $(CH_3)_3SiOCH_2(CF_2)_2OCF(CF_3)CF_2OCF(CF_3)CH_2OSi(CH_3)_3$ was added, and the mixture was heated at 55° C. for 18 h. $^{19}F$ NMR analysis showed the ratio of internal ring $CF_2$ signal to terminal ring $CF_2$ signal=13.7/1. Size exclusion showed $\overline{M}_n=6900$, $\overline{M}_w=9000$.

EXAMPLE 24

Polymerization of
$CF_3CF=CFOCH_2(CF_2)_2OCF(CF_3)CF_2OCF(CF_3)CH_2OCF=CFCF_3$ with
$(CH_3)_3SiOCH_2(CF_2)_2OCF(CF_3)CF_2OCF(CF_3)CH_2OSi(CH_3)_3$ A solution of $CF_3CF=CFOCH_2(CF_2)_2OCF(CF_3)CF_2OCF(CF_3)CH_2OCF=CFCF_3$ (2.894 g, 4.11 mmol) in glyme (15 mL) at 20° C. was treated with cesium fluoride (40 mg) and $(CH_3)_3SiOCH_2(CF_2)_2OCF(CF_3)CF_2OCF(CF_3)CH_2OSi(CH_3)_3$ (2.42 g, 4.11 mmol). The mixture was stirred for 18 h. An additional 0.24 g of $(CH_3)_3SiOCH_2(CF_2)_2OCF(CF_3)CF_2OCF(CF_3)CH_2OSi(CH_3)_3$ was added, and the mixture was stirred for 18 h. The mixture was diluted with glyme (50 mL), filtered, and evaporated to give 4.20 g of residue. $^{19}F$ NMR (THF-$d_8$): −66.9 and −67.8 (m, a=26), −78.5 to −83.8 (m's, a=112), −123.7 and −123.9 (overlapping s, a=22), −135.0 (m, a=9), −145.0 (m, a=10), −178.2 to −181.0 (m's, a=7), −184.0 and −186.0 (m's, a=1). $^1H$ NMR: 4.95 to 4.4 (m's), with trace signals at 4.4–4.2. Both spectra are in accord with polymer consisting of 1,1-disubstituted olefinic units. Size exclusion chromatography showed the major portion of the product with $\overline{M}_n=11,000$. The data are consistent with a polymer of the structure

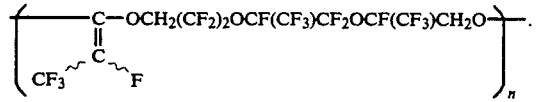

EXAMPLE 25

Polymerization of
$CF_3(F)C=C(CF)_3OCH_2(CF_2)_2OCF(CF_3)CF_2OCF(CF_3)CH_2OC(CF_3)=C(F)CF_3$ with
$(CH_3)_3SiOCH_2(CF_2)_2OCF(CF_3)CF_2OCF(CF_3)CH_2OSi(CH_3)_3$ A solution of $CF_3(F)C=C(CF)_3OCH_2(CF_2)_2OCF(CF_3)CF_2OCF(CF_3)CH_2OC(CF_3)=C(F)CF_3$ (1.12 g. 1.39 mmol) in glyme (15 mL) was treated with cesium fluoride (30 mg) and $(CH_3)_3SiOCH_2(CF_2)_2OCF(CF_3)CF_2OCF(CF_3)CH_2OSi(CH_3)_3$ (0.81 g, 1.38 mmol). After 19 h at ambient temperature, ether was added, and the mixture was filtered and evaporated to give 1.80 g of crude product. IR (thin film): 1698 (v.

weak), 1667 cm$^{-1}$ (C=C). Low-boiling impurities [mainly the cyclic, 1/1 adduct from perfluoro-2-butene and (CH$_3$)$_3$SiOCH$_2$(CF$_2$)$_2$OCF(CF$_3$)CF$_2$OCF(CF$_3$)CH$_2$OSi(CH$_3$)$_3$ present in the sample of CF$_3$CF=CFOCH$_2$(CF$_2$)$_2$OCF(CF$_3$)CF$_2$OCF(CF$_3$)CH$_2$OCF=CFC$_3$] were removed by kugelrohr distillation. $^{19}$F NMR (THF-d$_8$) of residue after kugelrohr distillation:: −63.5 to−65.8 (m's, combined a=84), −78.5 to −83.6 (m's, a=154), −123.5, −123.9, and −124.5 (m's, combined a=30), −135.8 (m, a=15), −144.9 (m, a=16). $^1$H NMR featured: 4.80 (t, J=11.4, a=10), 4.60 (d, J=12.8), and 4.48 (t, J=12.0, combined a=42). Trace signals were observed at 4.95, 4.2, and 4.05. Size exclusion chromatography showed the bulk of proudct with $\overline{M}_n$=5500. The data are consistent with a polymer of the structure.

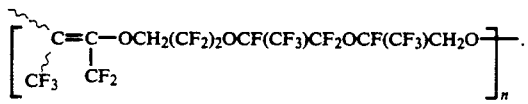

Also present was a component with $\overline{M}_n$=1000, which suggests the formation of cyclic dimer, C$_{26}$H$_8$F$_{40}$O$_8$, (mol wt=1208).

EXAMPLE 26

Polymerization of (CF$_3$)$_2$C=C(CF$_2$CF$_3$)OCH$_2$(CF$_2$)$_2$OCF(CF$_3$)CF$_2$OCF(CF$_3$)CH$_2$OC(CF$_2$CF$_3$)=C(CF$_3$)$_2$ with (CH$_3$)$_3$SiOCH$_2$(CF$_2$)$_2$OCF(CF$_3$)CF$_2$OCF(CF$_3$)CH$_2$OSi(CH$_3$)$_3$ A mixture of (CF$_3$)$_2$C=C(CF$_2$CF$_3$)OCH$_2$(CF$_2$)$_2$OCF(CF$_3$)CF$_2$OCF(CF$_3$)CH$_2$OC(CF$_2$CF$_3$)=C(CF$_3$)$_2$ (2.00 g, 2.0 mmol) and (CH$_3$)$_3$SiOCH$_2$(CF$_2$)$_2$OCF(CF$_3$)CF$_2$OCF(CF$_3$)CH$_2$OSi(CH$_3$)$_3$ (1.18 g, 2.0 mmol) was treated with TPS benzoate (50 mg). The mixture was heated to 50° C., but TMSF was not produced at a significant rate. The mixture was cooled to 25° C. and TASF (50 mg) was added. The viscous mixture was agitated occasionally over a two hour period until TMSF evolution was complete. $^{19}$F NMR (THF-d$_8$) of the soluble poriton was complex, and the major difference, by comparison with NMRs of the starting components, was a significant diminution of the signal intensity for the allylic CF$_2$ moieties. The residue was treated repeatedly with warm glyme to give a tacky, solid elastomer (1.23 g), and 1.19 g of residue after evaporation of solvent from the solvent fraction. Size exclusion chromatography of the soluble fraction showed starting material and low DP oligomers with $\overline{M}_n$=1500 to 3000. IR showed 1684 and 1646 cm$^{-1}$ (C=C). The data are consistent with a polymer of the structure.

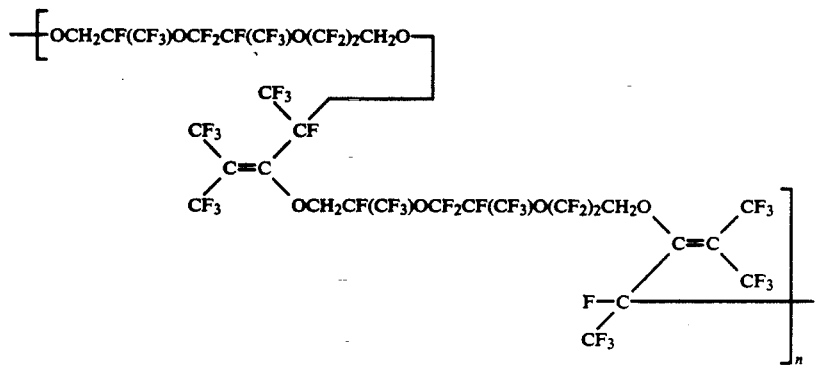

EXAMPLE 27

Polymerization of (CF$_3$)(F)C=C(F)OCH$_2$(CF$_2$)$_2$O[CF(CF$_3$)CF$_2$O]$_2$CF(CF$_3$)CH$_2$OC(F)=C(F)CF$_3$ with (CH$_3$)$_3$SiOCH$_2$(CF$_2$)$_3$CH$_2$OSi(CH$_3$)$_3$ A solution of (CF$_3$)(F)C=C(F)OCH$_2$(CF$_2$)$_2$O[CF(CF$_3$)CF$_2$O]$_2$CF(CF$_3$)CH$_2$OC(F)=C(F)CF$_3$ (1.74 g, 2.0 mmol) in glyme (20 mL) at −30° C. was treated with cesium fluoride (65 mg) and the (CH$_3$)$_3$SiOCH$_2$(CF$_2$)$_3$CH$_2$OSi(CH$_3$)$_3$ (0.71 g, 2.0 mmol). The mixture was warmed slowly to 0° C. and stirred or 2.5 h. $^{19}$F NMR analysis revealed complete conversion of trimethylsilyl ether end groups to trimethylsilylfluoride. The mixture was diluted with ether (30 mL), filtered, and evaporated to give 2.03 g of colorless, viscous oil. IR showed a trace absorption at 1768 cm$^{-1}$ (characteristic of 1,1-dialkoxysubstituted HFP derivatives), and a large envelope with maximum absorptions at 1368, 1308, 1243, 1160, and 1080 cm$^{-1}$. $^{19}$F NMR (THF-d$_8$): −66.8 (m, a=3), −67.8 (m, 2=6), −78.2 to 84.0 (m's, a=116), −120.5 (m, a=26), −123.7 (m, a=16), −125.0 (m, a=14), −134.5 (m, a=7), −145.0 (m, a=14), −180.5 and −181.0 (m's, a=8), −179.1 and −184.0 (m's, a=2). $^1$H NMR: 5.0 to 4.6 (m's), with trace signals at 5.1-5.0 and 4.4-4.2. Both spectra are in accord with polymer consisting of 1,1-disubstituted olefinic units. The data are consistent with a polymer of the structure

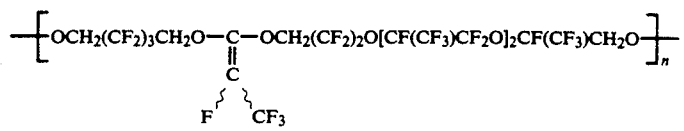

Size exclusion chromatography showed partially resolved bands with $\overline{M}_n$ ranging from 930 to 7800. The product was subjected to kugelrohr distillation which provided 0.39 g of colorless, viscous oil. $^1$H NMR (THF-d$_8$): 4.59 (t, J=14 Hz) and 4.60 (t, J=14 Hz, combined a=60), 4.73 (d, J=14.6) and 4.74 d, J=14.5 Hz, combined a=55), 4.98 to 4.78 (m, a=90). GC/MS showed one major component with parent ion of m/z=1042, M-F=1023, and M-(CF$_3$)=973, consistent with the cyclic 1:1 adduct.

EXAMPLE 28

Polymerization of

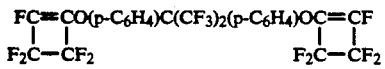

with p-(CH$_3$)$_3$SiOC$_6$H$_4$C(CF$_3$)$_2$C$_6$H$_4$OSi(CH$_3$)$_3$-p

A solution of C$_4$F$_5$O(p-C$_6$H$_4$)C(CF$_3$)$_2$(p-C$_6$H$_4$(C$_4$F$_5$ (3.10 g, 5.0 mmol) and P-(CH$_3$)$_3$SiOC$_6$H$_4$C(CF$_3$)$_2$C$_6$-H$_4$OSi(CH$_3$)$_3$-p (2.40 g, 5.0 mmol) in glyme (20 mL) at 19° C. was treated with TPSF (50 mg). The exothermic reaction caused the temperature to increase to 26° C. The mixture was heated at 50° C. for 2.0 h, and then 75° C. for 0.5 h. The cooled mixture was filtered to provide 0.53 g of white solid, identified as the cyclic dimer (vide infra). Evaporation of solvent provided 4.42 g of residue. $^{19}$F NMR (THF-d$_8$): −63.8 (s, a=137), −115.6 (s, a=70), −117.1 (m, a=3.5), −119.0 (m, a=3.5), −130.4 (m, a=2), consistent with polymer of DP=21 (M$_n$=9600). IR (KBr wafer): 1760 cm$^{-1}$ (minor), 1728 (C=C), 1610 and 1512 cm$^{-1}$. Size exclusion chromatography showed the major of product with $\overline{M}_n$=10,1000 in good agreement with the NMR estimate. The data are consistent with a polymer of the structure:

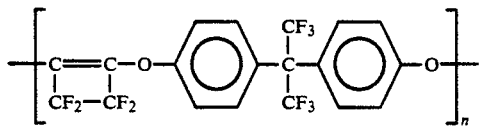

The cyclic dimer was characterized as follows. High resolution mass spectrum showed 916.35 (calcd for C$_{38}$H$_{16}$F$_{20}$O$_4$=916.07. A sample was sublimed at 210° C./0.04 mm to give mp=335°-339° C. (sealed capillary). $^{19}$F NMR (THF-d$_8$): −63.70 (s, 12F), −115.85 (s, 8F). Anal. Calcd for C$_{38}$H$_{16}$F$_{20}$O$_4$: C, 49.80; H, 1.76; F, 41.46. Found: C, 49.41; H, 1.83; F, 41.65.

EXAMPLE 29

Polymerization of

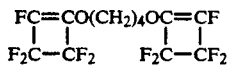

with (CH$_3$)$_3$SiO(CH$_2$)$_4$OSi(CH$_3$)$_3$

A solution of C$_4$F$_5$O(CH$_2$)$_4$OC$_4$F$_5$ (19 mmol) in propylene carbonate (15 mL) was treated with cesium fluoride (200 mg) and (CH$_3$)$_3$SiO(CH$_2$)$_4$OSi(CH$_3$)$_3$ (4.0 mL, 16 mmol). The mixture was heated to 85° C. for 1.5 h, cooled and treated with another portion (3 mmol) of (CH$_3$)$_3$SiO(CH$_2$)$_4$OSi(CH$_3$)$_3$. After 16 h at 80° to 85° C., $^{19}$F NMR analysis of the crude mixture showed: −113.2 (brd s, area=80), −145.9 (m, area=1), consistent with perfluorocyclobutenyl-ended polymer. A sample was subjected to high vacuum to remove solvent. $^1$H NMR (CDCl$_3$) showed propylene carbonate residues, OCH$_2$ and OCH$_2$CH$_2$ resonances, and only a trace Me$^3$Si signal. Size exclusion chromatography showed a major component with $\overline{M}_w$=2600, $\overline{M}_n$=1750. The data are consistent with a polymer of the structure

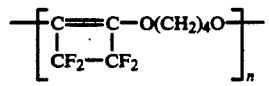

EXAMPLE 30

Polymerization of

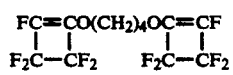

with (CH$_3$)$_3$SiO(CH$_2$)$_4$OSi(CH$_3$)$_3$

A solution of C$_4$F$_5$O(CH$_2$)$_4$OC$_4$F$_5$ (1.87 g, 5.00 mmol) and (CH$_3$)$_3$SiO(CH$_2$)$_4$OSi(CH$_3$)$_3$ (1.11 g, 4.75 mmol) in glyme (15 mL) was treated with a solution of TPSF (48 mg in 0.5 mL glyme). The mixture was heated slowly (ca. 0.5 h) to 65° C., then to 85° C. and stirred for 16 h. 19F NMR (THF-d$_8$/F11) of the crude mixture showed: −112.8 (m, area=111, CF$_2$ groups of internal rings), −116.1 (m, area=9) and −119.5 (m, area=9, CF$_2$ groups of terminal rings), −142.5 (m, area=4.5, vinyl F). Integration indicated the average number of internal rings/chain=12.3. Size exclusion chromatography showed the major fraction of the polymer with $\overline{M}_n$=5000, in reasonable agreement with $^{19}$F NMR analysis. Removal of solvent under vacuum gave 2.30 g of viscous residue. The data are consistent with a polymer of the structure

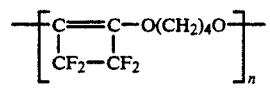

EXAMPLE 31

Polymerization of

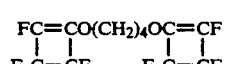

with (CH$_3$)$_3$SiO(CH$_2$)$_4$OSi(CH$_3$)$_3$ (A) Polymerization. A solution of C$_4$F$_5$O(CH$_2$)$_4$OC$_4$F$_5$ (3.74 g, 10.0 mmol) and (CH$_3$)$_3$SiO(CH$_2$)$_4$OSi(CH$_3$)$_3$ (2.34 g, 10.0 mmol) in glyme (20 mL) was treated with a solution of TPSF (100 mg in 1.0 mL glyme). The mixture was heated slowly to 85° C. and stirred for 18 h. $^{19}$F NMR analysis of the crude mixture showed (THF-d$_8$/F11): −112.7 (m, area=81, CF$_2$ groups of internal rings), −115.9 (m, area=3) and −119.2 (m, area=3, CF$_2$ groups of terminal rings), −142.2 (m, area=1.5, vinyl F). Integration indicated the average number of internal rings/chain=27, or $\overline{M}_n$=6100. Size exclusion chromatography showed the major fraction of the polymer with $\overline{M}_w=5170$, $\overline{M}_n=5120$, in good agreement with $^{19}$F NMR analysis. The data are consistent with a polymer of the structure

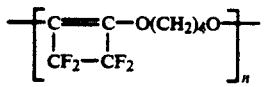

B) Cyclic Dimer. Evaporation of solvent and treatment of the residue with ether gave a small amount of crystalline solid. GC/MS analysis showed one component with M$^+$ of m/z=424.0887 (calcd for $C_{16}H_{16}F_8O_4$=424.0920), consistent with a macrocyclic structure containing two repeat units.

EXAMPLE 32

Polymerization of

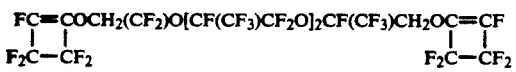

with $(CH_3)_3SiOCH_2(CF_2)_3CH_2OSi(CH_3)_3$ (A) Polymerization. A solution of $C_4F_5OCH_2(CF_2)O[CF(CF_3)CF_2O]_2CF(CF_3)CH_2OC_4F_5$ (1.83 g, 2.05 mmol) and $(CH_3)_3SiO(CF_2)_3CH_2OSi(CH_3)_3$ (0.729 g, 2.05 mmol) in glyme (20 mL) was treated with TPSF (35 mg in ca.0.5 mL glyme), and an exothermic reaction took place. After 18 h at ambient temperature, another 0.07 g of $(CH_3)_3SiOCH_2(CF_2)_3CH_2OSi(CH_3)_3$ was added and the mixture was stirred for 20 h. A third addition of $(CH_3)_3SiOCH_2(CF_2)_3CH_2OSi(CH_3)_3$(0.07 g) was added and the mixture was stirred for 18 h. A fourth addition of $(CH_3)_3SiOCH_2(CF_2)_3CH_2OSi(CH_3)_3$ (0.04 g) was made and the reaction was stirred for 48 h. Evaporation gave 2.30 g of very viscous resin. IR (thin film): 1752 cm$^{-1}$ internal C=C). $^1$H NMR (THF-d$_8$): 4.98 (d, J=12 Hz, a=11), 4.85 (m, a=29), 4.4 (minor m, a=6). $^{19}$F NMR: $-78.25$ to $-83.3$ (m's, a=117), $-114.7$ (m, a=54), $-117.2$ (m, a=1), $-119.8$ (m, a=1), $-121.0$ (m, a=34), $-124.0$ (m, a=16), $-125.0$, $-125.3$, and $-126.2$ (singlets, combined a=20), $-135.4$ (m, a=7), $-138.4$ (m, a=1), $-145.0$ (m, a=15). Size exclusion chromatography showed a set of bands with $\overline{M}_n=6200$. The data are consistent with a polymer of the structure

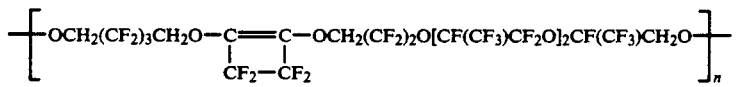

B) Cyclic Dimer. A significant fraction (ca. 25%) of material was eluted later and corresponded to $\overline{M}_w=1000$. This product was identified as the macrocycle $C_{25}H_8F_{34}O_7$ (n=1) by GC/MS which showed a very intense parent ion measured as 1067 (not accurately calibrated; theory=1066).

EXAMPLE 33

Polymerization of$(CH_3)_3SiOCH_2(CF_2)_3CH_2OSi(CH_3)_3$ with Perfluorocyclobutene A solution of $(CH_3)_3SiOCH_2(CF_2)_3CH_2OSi(CH_3)_3$ (8.0 g, 22.5 mmol) in glyme (25 mL) at 5° C. was treated with TPSF (100 mg) in glyme (0.5 mL). Perfluorocyclobutene (8.1 g, 50 mmol) was added rapidly, while the temperature was controlled between 0° C. to 15° C. with a dry-ice bath. After 3 h, most of the volatiles were removed under vacuum, and the residue was partitioned with F$_{113}$ (250 mL). The portion which did not dissolve readily was saved separately to give 3.85 g of foam after evaporation of solvent. IR (thin film): 1752 cm$^{-1}$ (C=C). $^{19}$F NMR (THF-d$_8$): $-114.7$ (s, a=13), $-116$ to $-117$ (m, a=10), $-119$ to $-121.5$ (m, a=52), $-125$ (m, a=25), $-138.3$ (m, a=1, vinyl F). Size exclusion chromatography showed the bulk of material with $\overline{M}_n=11,400$. The data are consistent with a polymer of the structure:

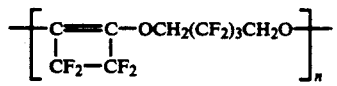

and the cyclic compounds also have the same repeat unit, where n is 2, 3 or 4.

Product which readily dissolved in F$_{113}$ was washed with water, dried, and evaporated to give 2.15 g of residue. Treatment of this residue with ether and petroleum ether gave a small amouint of crystalline solid. $^{19}$F NMR (THF-d$_8$): $-114.5$ (s, ring CF$_3$), $-120.6$ (m, CH$_2$CF$_2$), $-125.1$ (s, central CF$_2$). GC analysis (method 1): one component at 14.16 min (97%). GC/MS showed one component with intense M$^+$ of m/z=668.0182 ($C_{18}H_8F_{20}O_4$), consistent only with the cyclic dimer. Crystals suitable for X-ray analysis were grown by slow cooling of a saturated ether solution of the dimer. Mass spectral analysis of a kugelrohr distilled sample indicated the presence of cyclic trimer (1001.87, calcd=1002.02), and cyclic tetramer (1335.8, calcd=1336.02).

EXAMPLE 34

Polymerization of$(CH_3)_3SiOCH_2(CF_2)_3CH_2OSi(CH_3)_3$ with Perfluorocyclobutene A solution of $(CH_3)_3SiOCH_2(CF_2)_3CH_2OSi(CH_3)_3$ (3.53 g, 10.0 mmol) in glyme (20 mL) at $-20°$ C. was treated with TPSF (50 mg) in glyme (0.5 mL). Perfluorocyclobutene (1.6 g, 10 mmol) was added rapidly, while the temperature was controlled between $-20°$ and 5° C. After 0.5 h at 15° C., $^{19}$F NMR analysis of the mixture revealed complete conversion of Me$_3$Si- groups to Me$_3$SiF. Removal of volatiles provided 3.38 g of colorless, viscous residue. IR (thin film): 1752 cm$^{-1}$ (C=C), with minor shoulder at 1765 cm$^{-1}$.$^{19}$F NMR (THF-d$_8$): $-114.7$ (s, a=13), $-117.0$ (m, a=11), $-119.7$ (m, a=9), $-120.5$ to $-120.9$ (m, a=105), $-125.3$ (s, a=52), $-138.5$ (m, a=4, vinyl F). Size exclusion chromatography showed the bulk of material with $\overline{M}_n=4300$, along with ca. 10% cyclic dimer. The data are consistent with the structure:

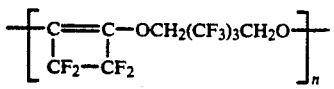

EXAMPLE 35

Polymerization of
(CH$_3$)$_3$SiOCH$_2$(CF$_2$)$_2$O[CF(CF$_3$)CF$_2$]$_2$CF(CF$_3$)CH$_2$Si(CH$_3$)$_3$ with Perfluorocyclobutene A solution of (CH$_3$)$_3$SiOCH$_2$(CF$_2$)$_2$O[CF(CF$_3$)CF$_2$O]$_2$CF(CF$_3$)CH$_2$OSi(CH$_3$)$_3$ (5.00 g, 6.63 mmol) in glyme (20 mL) at 0° C. was treated with TPSF (50 mg) in glyme (0.5 mL). Perfluorocyclobutene (2.5 g, 15 mmol) was added rapidly, and the temperature was increased to −12° C. After 0.5 h at 20° C., $^{19}$F NMR analysis of the mixture revealed complete conversion of Me$_3$Si groups to Me$_3$SiF. Removal of volatiles provided 5.1 g of light yellow, viscous residue. A 2.0 g sample was kugelrohr distilled to give 0.67 g colorless oil, bp 85° C./0.07 mm, and 1.25 g of pot residue. IR (distilled sample): 1767 cm$^{-1}$ (C=C). $^{19}$F NMR featured (THF-d$_8$): −78 to −84.5 (m, a=145), −117.3 (m, a=29), −120.0 (m, a=26), −123.7 (m, a=12), −135.5 (m, a=8), −138.0 and −138.7 (m's of equal area=13), −145.0 (m, a=15), consistent with the bis(vinyl) ether as the major component. $^1$H NMR features: 5.17 (d, J=12.3 Hz), and 5.03 (t, J=12.3 Hz). $^{19}$F NMR of the pot residue: −79.0 to −83.4 (m's, a=121), −114.8 (s, a=13), −117.2 (m, a=10), −120.0 (m, a=10), −123.6 (s) and −124.0 (s, a=13), −135.0 (m, a=7), −138.0 and −138.6 (m's, a=5), −145.0 (m, a=15), consistent with the linear dimer end-capped by perfluorocyclobutene as the average length structure. Size exclusion chromatography showed unresolved oligomers with $\overline{M}_n$ 4100 to 1200 (n=2 to 5). $^1$H NMR featured: 5.17 (d, J=12 5) and 5.04 (t, J=12.5), 4.97 (d, J=12), and 4.80 (t, J=12). Comparison with the spectrum of the C$_4$F$_5$OCH$_2$(CF$_2$)$_2$O[CF(CF$_3$)CF$_2$O ]$_2$CF(CF$_3$)CH$_2$O C$_4$F$_5$ showed that the highest-field signals correspond to CH$_2$ groups close to internal rings (bearing two oxygen substituents). The data are consistent with a polymer of the structure:

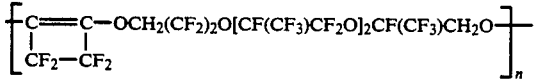

EXAMPLE 36

One-step Polymerization of
(CH$_3$)$_3$SiO(CH$_2$)$_4$OSi(CH$_3$)$_3$ with Perfluorocyclobutene A solution of (CH$_3$)$_3$SiO(CH$_2$)$_4$OSi(CH$_3$)$_3$ (4.60 g, 19.6 mmol) in THF (15 mL) was treated with a solution of TPSF (50 mg) in THF (1 mL) by syringe. Perfluorocyclobutene (3.09 g, 19 mmol) was added slowly over a 40 min period, while the temperature was maintained at 25°-29° C. The mixture was heated at 75° C. for 48 h. $^{19}$F NMR (THF-d$_8$): −113. (m, area=81), −116.1 (m, area=33), −119.5 (m, area=32), −142.5 and −142.9 (m's, area=16), consistent with an average DP=4.5, with vinyl end groups. Further analysis was not carried out with this sample. Evaporation gave 2.24 g of yellow, viscous liquid. The data are consistent with the structure:

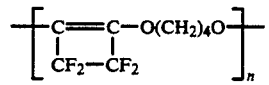

EXAMPLE 37

Polymerization of (CH$_3$)$_3$SiO(CH$_2$)$_4$OSi(CH$_3$)$_3$ with Perfluorocyclopentene A mixture of (CH$_3$)$_3$SiO(CH$_2$)$_4$OSi(CH$_3$)$_3$ (4.69 g, 20 mmol) and propylene carbonate (20 mL) was treated with perfluorocyclopentene (4.2 g, 20 mmol) and then with cesium fluoride (200 mg). The temperature rose steadily from 21° to 42° C. After stirring at room temperature for 2 h, volatiles were removed under vacuum (0.05 mm) using temperatures up to 95° C. There remained 5.5 g of viscous residue. $^1$H NMR of this portion showed broad multiplets at 4.25 and 1.80, and contained no MeSi signals. $^{19}$F NMR exhibited: −111.2 to −112.5 (m's, area=112), −115 3 (m, area=43), −116.7 (m, area=42), −127.1 (m, area=15), −129.8 (m, area=60), −130.1 (s, area=42), −162.5 (m, area=21), consistent with oligomers of average DP=4 containing perfluorocyclopentenyl end groups. Size exclusion chromatography showed one major component with M$_w$=1700, Mn=1200. IR (thin film) featured: 1750, 1725 and 1685 cm$^{-1}$. The data are consistent with a polymer of the structure

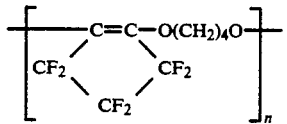

EXAMPLE 38

Fluorination of

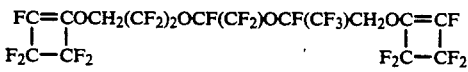

A solution of C$_4$F$_5$OCH$_2$(CF$_2$)$_2$OCF(CF$_3$)CF$_2$OCF(CF$_3$)CH$_2$OC$_4$F$_5$ (2.59 g, 3.56 mmole) in F113 (370 mL) was placed in a translucent FEP reactor equipped with a stainless steel head. The reaction mixture was treated with elemental fluorine diluted with nitrogen (5% to 50% F$_2$) over a 2.3 hr period; total # mmol F$_2$ used=53.4. After 33% of the fluorine had been added, an ultraviolet lamp (Sylvania #RSM 275 watt sunlamp) positioned outside the reactor, was directed at the reactor and was turned on for the remainder of the experiment. The resulting solution was purged with nitrogen, treated with sodium fluoride to remove HF, and filtered. Evaporation gave 3.40 g of colorless oil which was kugelrohr distilled to provide 1.76 g bp 43°-60° C. (0.1 mm), and 0.39 g, bp 80°-108° C. GC analysis (method 1) showed ca. 92% purity and a yield of ca 70%, $^{19}$F NMR (F11): −80.0 to −83.8 (m, 14 F, CF$_3$+OCF$_2$), −129.01 (s, 2F, CF$_2$), −131.15 and −134.19 (AB pattern, J$_{AB}$=23Q Hz, 8F, ring CF$_2$CF), −133.5 (unresolved m, 4F), −140.36 and −140.84 (m's, 1F each, ring CF), −145.2 (m, 2F, FC(CF$_3$)) COSY experiment showed major coupling patterns with ring CF$_a$F$_b$ groups, CF$_3$ to CF, and OCF$_2$ to ring CF.

GC/MS showed the major component with highest observed mass of m/e=694.9561770, corresponding to M-($C_4F_7$) (Calcd for $C_{13}F_{25}O_4$=694.939735. Also observed were 528.9586 (calcd for M-[$C_4F_7+C_3F_6O$]=528.954402) and 362.9704900 (calcd for M-[$C_4F_7+C_3F_6O+C_3F_6$]=362.969069). The data are consistent with a compound of the formula

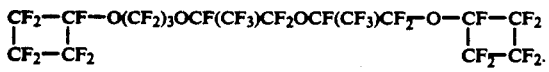

A 0.59 g sample of higher boiling material (127°-133° C. @0.1 mm) was obtained. GC/MS data (negative ion) were consistent with a dimeric structure of composition $C_{34}F_{62}O_8$; highest observed mass=1532.8231200 ($C_3DF_{55}O_8$=1532.871485; assignment=M-($C_4F_7$); 1366.8830570 ($C_{27}F_{49}O_7$=1366.886152; assignment =M-[$C_4F_7+C_3F_6O$]).

EXAMPLE 39

Fluorination of
$(CF_3)_2C = C(CF_2CF_3)OCH_2(CF_2)_2OCF(CF_3)C-F_2OCF(CF_3)CH_2OC(CF_2CF_3) = C(CF_3)$ A solution of $CF_3(CF_3)C = C(CF_2CF_3)OCH_2(CF_2)_2OCF(CF_3)CF_2OCF(CF_3)C-H_2OC(CF_2CF_3) = C(CF_3)_2$ (5.00 g. 4.98 mmol) in F113 (370 mL) was placed in a translucent Teflon® FEP reactor equipped with a stainless steel head and treated with elemental fluorine diluted with nitrogen (5 to 50% $F_2$ over a 2.0 hr period; total # mmol $F_2$ used=59.8). After 28% of the fluorine had been added, the ultraviolet lamp was turned on for the remainder of the experiment. The resulting solution was purged with nitrogen, treated with sodium fluoride to remove HF, and filtered. Evaporation gave 5.81 g of colorless oil which was kugelrohr distilled to provide 5.01 g bp 70°-75° C. (0.1 mm); bp (1 atmosphere) ca. 260° C. GC analysis (method 1) showed two groups of components (61% and 22% of total area). $^{19}F$ NMR (neat): $-71.3$ and $-71.6$ (m's, a=17) and $-72.8$ (s, a=16, terminal $(CF_3)_2$ groups), $-75.5$ to $-82.0$ (brd m's) and $-80.84$, $-80.96$, $-81.19$ (singlets, combined a=64, $OCF_2+CF_3$), $-116.0$ to $-121.5$ (m's, a=10, $CF_2$), $-128.6$ (s, a=6, internal $CF_2$), $-133.2$ and $-133.6$ (m's, combined a=5.3, CFO), $-145.0$ (m, a=6.2, internal CF), $-181.5$ and $-181.8$ (m's, a=5.1, terminal CF). GC/MS (negative ion) showed the major component (no isomer separation on this column) with highest observed mass of m/z=832.9291080, corresponding to M-($C_6F_{13}$) calcd for $C_{15}F_{31}O_4$=832.930153. Also observed were 666.9434200 (calcd for M-[$C_4F_{13}+C_3F_6O$]=666.9444820) and 500.9594120 (calcd for M-[$C_6F_{13}+2C_3F_6O$]=500.959487). The data are consistent with a compound of the formula

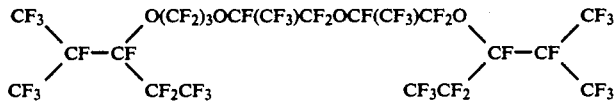

EXAMPLE 40

Fluorination of Polymer from Example 25

A solution of the polymer as prepared in Example 25 (0.89 g, 1.5 m equiv) in $F_{113}$ (370 mL) was placed in a translucent Teflon® FEP reactor equipped with a stainless steel head and treated with elemental fluorine diluted with nitrogen (5 to 50% $F_2$ over a 2.0 hr period; total # mmol $F_2$ used=18). After 33% of the fluorine had been added (1.0 hr), the ultraviolet lamp was turned on for the remainder of the reaction. The resulting solution was purged with nitrogen, treated with sodium fluoride to remove HF, and filtered. Evaporation gave 1.13 g of viscous oil. IR (thin film) featured a large absorption envelope 1300-1100 cm$^{-1}$; C=C band of the starting vinyl polymer was absent. Anal. calcd for $C_{13}F_{26}O_4$: C, 21.87; F, 69:17; O, 8.96. Found: C, 22.37; F, 69.22; H, 0.26. The data are consistent with the structure:

with no olefinic groups or hydrogen remaining.

EXAMPLE 41

Fluorination of Polymer from Example 16

A solution of the polymer as prepared in Example 16 ($\overline{M}_n$=17,400) (6.49 g, 10.7 mequiv) in F113 (370 mL) was placed in a translucent Teflon® FEP reactor equipped with a stainless steel head and treated with elemental fluorine diluted with nitrogen (5 to 50% $F_2$ over a 3.0 hr period; total # mmol $F_2$ used=130). After 28% of the fluorine had been added (1.0 hr), the ultraviolet lamp was turned on for the remainder of the reaction. The resulting mixture was purged with nitrogen and filtered to remove 2.18 g of white solid. The solution was treated with sodium fluoride and filtered. Evaporation gave 4.24 g of very viscous oil. $^{19}F$ NMR (neat, 100° C.): $-78.0$ to $-85$ (m, a=97), $-123$ to $-134.5$ (m,. a=38), $-137.0$ and $-138.5$ to $-140.0$ (m, a=8), $-143.5$ (m, a=12), $-145.2$ (m, a=12), in accord with the desired material based upon spectral analysis of the fluorination product from $C_4F_5OCH_2(CF_2)_2OCF(CF_3)CF_2OCF(CF_3)CH_2OC_4F_5$. Anal. Calcd for $C_{13}F_{24}O_4$: C, 23.09; F, 67.44. Found: C, 22.98; F, 67.23. The solid material was submitted for analysis also. Found: C, 23.40, 23.20; F, 67.12, 67.00. The data are consistent with a polymer of the structure

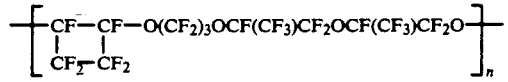

with no hydrogen or olefinic groups remaining.

EXAMPLE 42

Fluorination of Cyclic Dimer from Example 14

A solution of the cyclic dimer as prepared in Example 14 (0.74 g, 0.65 mmol) in $F_{113}$ (370 mL) was placed in a translucent Teflon® FEP reactor equipped with a stainless steel head and treated with elemental fluorine diluted with nitrogen (5 to 50% $F_2$ over a 2.0 hr period; total # mmol $F_2$ used=17.7). When 33% of the fluorine had been added (40 min), the ultraviolet lamp was turned on for the remainder of the reaction. The resulting mixture was purged with nitrogen, treated with sodium fluoride, and filtered. Evaporation gave 0.95 g of colorless oil which was kugelrohr distilled to provide 0.59 g, bp 90°-150° C. (0.1 mm). GC/MS (negative CI) showed the major coponent characterized by a parent ion of m/z=1351.889450 (calcd for $C_{26}F_{48}O_8 = 1351.882664$), next-highest mass=1170.8878170 (calcd for $C_{22}F_{41}O_x = 1170.893843$. M-($C_4F_6$+F) next-highest mass=1004.9139250 (calcd for $C_{19}F_{35}O_7 = 1004.908510$, M-[$C_4F_6$+F+$C_3F_6O$]). $^{19}F$ NMR (F11): −78.0 to −88.0 (m, a=60), −122.0 (m, a=3.5), −125.0 to −133.0 (m, a=20), −138.0 to −140.0 (m, a=2.5), −145.0 (m, a=7). The data are consistent with a compound of the formula

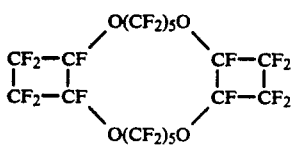

B. Preparation of Macrocycle

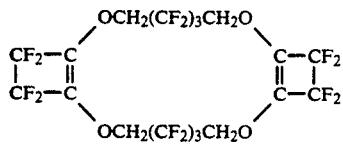

A solution of

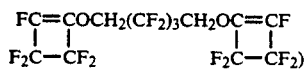

(4.96 g., 10.0 mmol) and $(CH_3)_3SiOCH_2(CF_2)_3C-H_2OSi(CH_3)_3$ in glyme (500 mL) at −20° C. was treated with CsF (200 mg). The mixture was warmed slowly to 25° C. and stirred for 18 hours. Another 120 mg of CsF and 0.6 g. of bis(silyl) ether were added and the mixture was stirred for 24 hours. 200 mL of ether was added and the mixture was filtered, evaporated and kugelrohr distilled to provide 3.48 g. of white solid, bp 124°-156° C. (0.1 mm). GC analysis showed two major products in a 3.7/1 ratio. GC/MS showed both components with parent ion of m/z=668. Recrystallization from ether gave 2.88 g which contained ca. 3% of the minor isomer. A second crystallization gave 2.27 g, mp=122°-123° C. with purity >99.8%. $^{19}F$ NMR (THF-$d_8$): −114.53 (s, 8F), 120.6 [m, 8F($CH_2CF_2$)], 125.06 (s, 4F); lineshapes were unchanged to −70° C. $^1H$ NMR: 4.85 (m, pseudotriplet, temperature independent to −85° C.).

EXAMPLE 43

Preparation of Macrocycle-Fluoride Adduct

A solution of macrocycle from Experiment 42B (446 mg, 0.67 mmol) in THF (3 mL) was added to a mixture of TAS trimethyldifluorosiliconate (184 mg, 0.67 mmol) and THF (5 mL). The resulting colorless solution was evaporated (ca. 1 mm) to give 571 mg of white solid, mp=108°-110° C. (dec). Further purification and crystal growth was carried out as follows. The solid was dissolved in 5 mL ether, and the soluble portion was pipetted into a clean vial and cooled at −25° C. A small volume of petroleum ether was added slowly, and the mixture was cooled for an additional 2 hrs. The mother-liquor was removed and the crystals were subjected to vacuum to remove remaining solvent. The melting (decomposition) point was unchanged. $^1H$ NMR (THF-$d_8$), 25° C.): 6.05 (brd m, $w_{\frac{1}{2}}$=43 Hz, 8H), 2.96 (s, 18 H). $^{19}F$ NMR (THF-$d_8$, 25° C.): −76.0 (brd s, 1F), −117.10 (s, 8F), −123.67 (s, 8F), −131.1 (s, 4F). X-ray crystallographic analysis showed the complex anion to be of $C_2$ symmetry, with the central fluoride held in place by four C-H-F interactions.

EXAMPLE 44

Group Transfer Polymerization of Methyl Methacrylate Using Macrocycle-Fluoride Adduct from Example 43 as Catalyst A solution of $(CH_3)_2C=C(OCH_3)OSi(CH_3)_3$ (0.62 g, 3.6 mmol) and methyl methacrylate (5.00 mL) in glyme (20 mL) was treated with a glyme (0.5 mL) solution of the macrocyclic anion from Example 43 (15 mg, 0.018 mmol). The temperature began to increase upon addition of the first few drops of catalyst, then rapidly increased to 56° C. After 1.0 hr at 25° C., a second portion of MMA (5.0 mL) was added. The temperature increased to 26° C. After 4.0 hrs. at 25° C., volatiles were removed to give 7.59 g of colorless, solid PMMA. GPC analysis revealed $\overline{M}_w$=4820, $\overline{M}_n$=2730, D=1.77.

Although the present invention has been described with reference to the particular embodiments herein set forth, it is to be understood that the present disclosure has been made only by way of example and that numerous changes in the details of the processes and compositions herein enumerated may be resorted to without departing from the spirit and scope of the invention should not be limited by the specification but only by the scope of the claims appended hereto.

What is claimed is:

1. A polymer consisting essentially of the repeat unit:

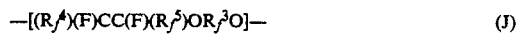

wherein wherein $R_f^3$ is a diradical of the formula —$C_xF_{2x}$—, x is an integer from 2 to 20, provided that when x is an integer from 4 to 20, some of the carbon atoms may be internally interrupted with oxygen atoms forming ether structures with the proviso that the oxygen atoms be separated by two or more carbon atoms; $R_f^4$ and $R_f^5$ are independently of the formula —$C_zF_{2z+1}$, z is an integer from 1 to 10; $R_f^4$ and $R_f^5$ taken together are —($CF_2$)—$_m$, and m is 2, 3 or 4, and wherein no olefinic unsaturation is present in the polymer.

2. A polymer consisting essentially of the following repeat unit:

wherein:

$R_f^3$ is a diradical of the formula —$C_xF_{2x}$—, wherein x is an integer from 2 to 20, provided that when x is an integer from 4 to 20, some of the carbon atoms may be internally interrupted with oxygen atoms forming ether structures with the proviso that the oxygen atoms be separated by 2 or more carbon atoms; and $R_f^4$ is —$C_zF_{2z+1}$, wherein z is an integer of 1 to 10.

3. A polymer consisting essentially of the repeat unit:

$$-[(R_f^1)C=C(R_f^2)ORO]- \qquad (A)$$

wherein R is:

a diradical of the formula —$C_xH_{2x-y}F_y$— wherein x is an integer from 2 to 20, y is 0 or an integer from 1 to 2x for a given value of x, with the additional proviso that the carbon atoms containing the free valence of the diradical not be attached to fluorine atoms, and when x is an integer of from 4 to 20 some of the carbon atoms may be internally interrupted with oxygen atoms forming ether structures with the proviso that the oxygen atoms be separated by 2 or more carbon atoms;

—$C_6H_{4-a}F_1$— wherein a is 0, 1, 2, 3 or 4, with the proviso that the radical bonds are not on adjacent carbon atoms;

—$C_{10}H_{6-b}F_b$— wherein b is 0 or an integer of 1 to 6, with the proviso that the radical bonds are not on adjacent carbon atoms;

—$C_{12}H_{8-c}F_c$— wherein c is 0 or an integer of 1 to 8, with the proviso that the radical bonds are not on adjacent carbon atoms; or —$C_6H_{4-d}$—$R^1$—$C_6H_{4-e}F_e$—, wherein d and e are independently 0 or an integer from 1 to 4, $R^1$ is —$C_xH_{2x-f}F_f$—, wherein f is 0 or an integer from 1 to 2x and x is an integer of 2 to 20; and $R_f^1$ and $R_f^2$ are independently —$C_zF_{2z+1}$, wherein z is an integer from 1 to 10; or $R_f^1$ and $R_f^2$ taken together in the cis configuration are —$(CF_2)_m$—, wherein m is 2, 3 or 4, with the proviso that when $R_f^1$ and $R_f^2$ taken together are —$(CF_2)_m$—, R is —$CH_2(CF_2)_2O[CF(CF_3)CF_2O]_h(CF_3)CH_2$—, wherein h is 0, 1, 2, 3, or 4.

4. The polymer of claim 3 wherein x is 4 to 20, and some of the carbon atoms are internally interrupted with oxygen atoms forming ether structures.

5. The polymer as recited in claim 3 wherein $R_f^1$ and $R_f^2$ are each independently —$C_zF_{2z+1}$.

6. A polymer consisting essentially of the repeat unit:

$$-[C(=CFR_f^1)OR^8O]- \qquad (B)$$

wherein:

$R_f^1$ is —$C_zF_{2z+1}$, wherein z is an integer from one to 10, and $R^8$ is a diradical of the formula —$C_xH_{2x-y}F_y$—, where x is an integer from 2 to 20, y is 0 or an integer from 1 to 2x, but with the proviso that the carbon atoms containing the free valences of the diradical not be attached to fluorine atoms, and when x is an integer of 4 to 20 some of the carbon atoms may be internally interrupted with oxygen atoms forming ether structures with the additional proviso that the oxygen atoms be separated by two or more carbon atoms;

—$C_6H_{4-a}F_1$— wherein a is 0, 1, 2, 3 or 4, with the proviso that the free valences are not on adjacent carbon atoms;

—$C_{10}H_{6-b}F_b$— wherein b is 0 or an integer of 1 to 6, with the proviso that the free valencies are not on adjacent carbon atoms;

—$C_{12}H_{8-c}F_c$— wherein c is 0 or an integer of 1 to 8, with the proviso that the free valences are not on adjacent carbon atoms; or —$C_6H_{4-d}$—$R^1$—$C_6H_{4-e}F_e$—, wherein d and e are independently 0 or an integer from 1 to 4, $R^1$ is —$C_xH_{2x-f}F_f$—, wherein f is 0 or an integer of 1 to 2x; and with the further proviso that in $R^8$ one of the carbon atoms adjacent to the carbon atoms containing the free valences of the diradical be attached to at least 2 fluorine atoms.

* * * * *

UNITED STATES PATENT AND TRADEMARK OFFICE
CERTIFICATE OF CORRECTION

PATENT NO. : 5,243,025

DATED : SEPTEMBER 7, 1993

INVENTOR(S) : WILLIAM BROWN FARNHAM AND MARIO JOSEPH NAPPA

It is certified that error appears in the above-identified patent and that said Letters Patent is hereby corrected as shown below:

Column 19, lines 52-53 replace
" $FC=COCH_2(CF_2)_2OCF(CF_3)CF_2OCF(CF_3)CH_2OC=CF$ "

$F_2C-CF_2$                                  $F_2C-CF_2$ with

-- $FC=COCH_2(CF_2)_2OCF(CF_3)CF_2OCF(CF_3)CH_2OC=CF$ --

| |                                                  | |

$F_2C-CF_2$                                $F_2C-CF_2$

Column 31, lines 10-11 replace:
"$(CH_3)_3SiOCH_2(CF_2)_2O[CF(CF_3)CF_2]_2CF(CF_3(CH_2)Si(CH_3)_3$ with perfluorocyclobutene "

with --$(CH_3)_3SiOCH_2(CF_2)_2O[CF(CF_3)CF_2O]_2CF(CF_3(CH_2)Si(CH_3)_3$ with perfluorocyclobutene --

UNITED STATES PATENT AND TRADEMARK OFFICE
CERTIFICATE OF CORRECTION

PATENT NO. : 5,243,025
DATED : SEPTEMBER 7, 1993
INVENTOR(S) : WILLIAM BROWN FARNHAM AND MARIO JOSEPH NAPPA

It is certified that error appears in the above-identified patent and that said Letters Patent is hereby corrected as shown below:

Column 32, lines 42-44 replace

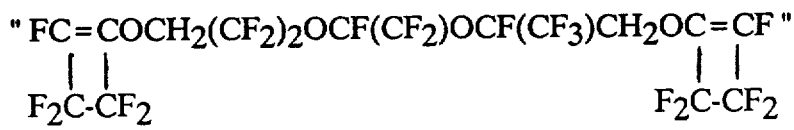

with

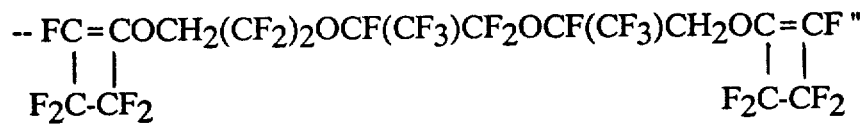

Signed and Sealed this

Fifth Day of July, 1994

Attest:

Attesting Officer

BRUCE LEHMAN

Commissioner of Patents and Trademarks